US010575809B2

United States Patent
(12) United States Patent
Akiyama et al.

(10) Patent No.: US 10,575,809 B2
(45) Date of Patent: Mar. 3, 2020

(54) X-RAY DIAGNOSIS APPARATUS

(71) Applicant: Toshiba Medical Systems Corporation, Otawara-shi (JP)

(72) Inventors: Masaki Akiyama, Otawara (JP); Kunio Shiraishi, Otawara (JP); Ko Fuchigami, Otawara (JP); Makoto Kaneko, Otawara (JP); Tadaharu Kobayashi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 192 days.

(21) Appl. No.: 15/659,015

(22) Filed: Jul. 25, 2017

(65) Prior Publication Data

US 2018/0021000 A1 Jan. 25, 2018

(30) Foreign Application Priority Data

Jul. 25, 2016 (JP) ................................ 2016-145624
Jul. 25, 2017 (JP) ................................ 2017-143787

(51) Int. Cl.
*A61B 6/06* (2006.01)
*A61B 6/00* (2006.01)

(52) U.S. Cl.
CPC .............. *A61B 6/5205* (2013.01); *A61B 6/06* (2013.01); *A61B 6/4441* (2013.01); *A61B 6/485* (2013.01); *A61B 6/504* (2013.01); *A61B 6/54* (2013.01)

(58) Field of Classification Search
CPC ........ A61B 6/5205; A61B 6/06; A61B 6/4441
See application file for complete search history.

(56) References Cited

U.S. PATENT DOCUMENTS

2014/0240355 A1* 8/2014 Isaacs ..................... G06T 11/60
345/633
2015/0139394 A1* 5/2015 Kang .................. A61B 6/5211
378/62

FOREIGN PATENT DOCUMENTS

| | | |
|---|---|---|
| JP | 2000-342565 | 12/2000 |
| JP | 2005-34259 | 2/2005 |
| JP | 2010-279594 | 12/2010 |
| JP | 2013-90965 | 5/2013 |
| JP | 2014-12216 | 1/2014 |

* cited by examiner

*Primary Examiner* — Hugh Maupin
(74) *Attorney, Agent, or Firm* — Oblon, McClelland, Maier & Neustadt, L.L.P.

(57) ABSTRACT

An X-ray diagnosis apparatus according to an embodiment acquires a first X-ray image and a second X-ray image by using mutually-different radiation doses; acquires a third X-ray image based on X-rays radiated onto a region of interest of the subject and onto a region other than the region of interest in mutually-different radiation doses; obtains position information of the region of interest; and on a basis of the position information, generates a subtraction image by calculating a difference between the region of interest in the third X-ray image and a region corresponding to the region of interest in the first X-ray image and calculating a difference between the region other than the region of interest in the third X-ray image and a region corresponding to the region other than the region of interest in the second X-ray image.

20 Claims, 9 Drawing Sheets

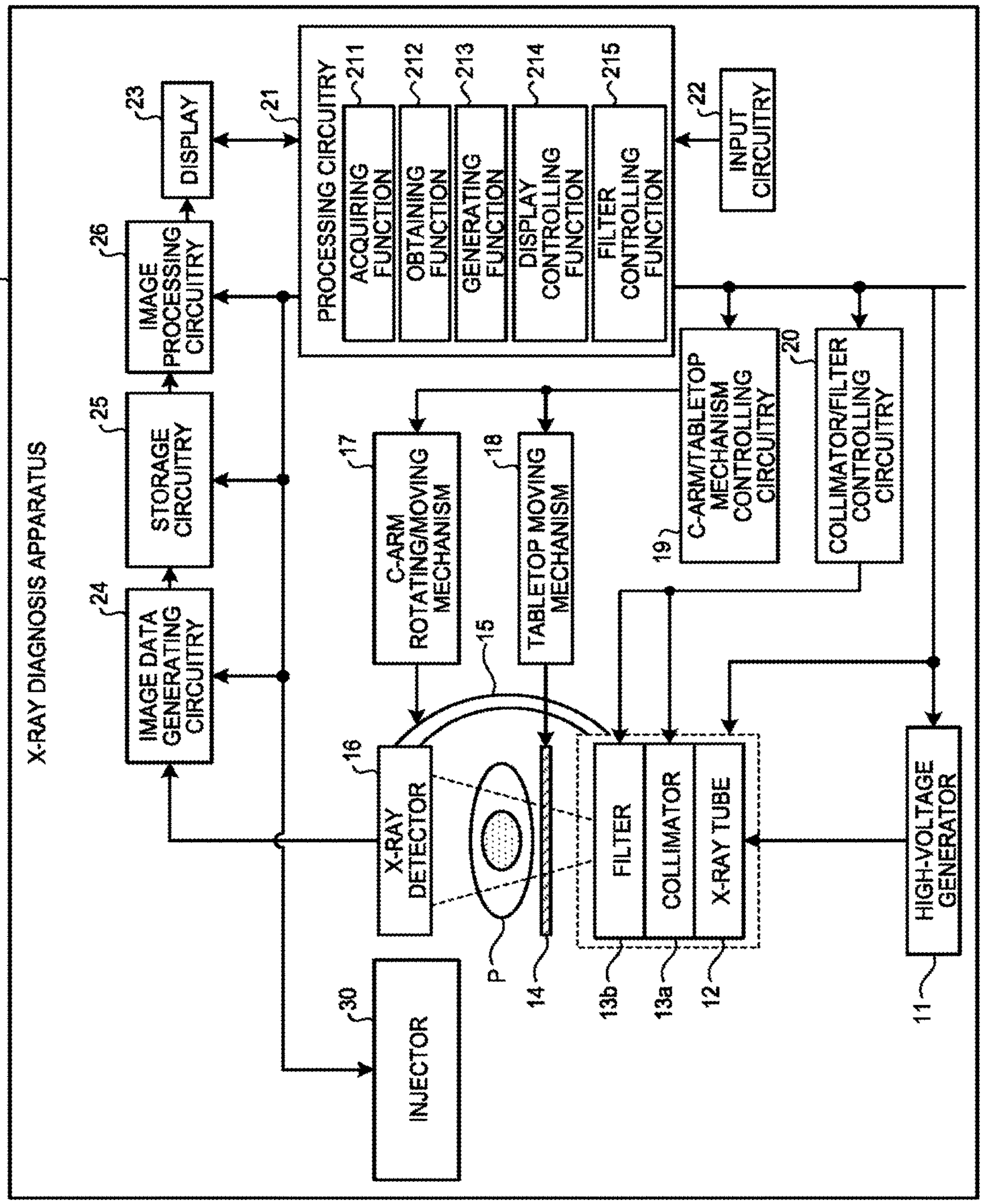
FIG.1
100
X-RAY DIAGNOSIS APPARATUS
24
IMAGE DATA GENERATING CIRCUITRY
25
STORAGE CIRCUITRY
26
IMAGE PROCESSING CIRCUITRY
23
DISPLAY
21
PROCESSING CIRCUITRY
211
ACQUIRING FUNCTION
212
OBTAINING FUNCTION
213
GENERATING FUNCTION
214
DISPLAY CONTROLLING FUNCTION
215
FILTER CONTROLLING FUNCTION
22
INPUT CIRCUITRY
17
C-ARM ROTATING/MOVING MECHANISM
18
TABLETOP MOVING MECHANISM
19
C-ARM/TABLETOP MECHANISM CONTROLLING CIRCUITRY
20
COLLIMATOR/FILTER CONTROLLING CIRCUITRY
15
16
X-RAY DETECTOR
FILTER
COLLIMATOR
X-RAY TUBE
HIGH-VOLTAGE GENERATOR
30
INJECTOR
P
14
13b
13a
12
11

X-RAY DIAGNOSIS APPARATUS

CROSS-REFERENCE TO RELATED APPLICATIONS

This application is based upon and claims the benefit priority from Japanese Patent Application No. 2016-145624, filed on Jul. 25, 2016, and Japanese Patent Application No. 2017-143787, filed on Jul. 25, 17; the entire contents of which are incorporated herein by reference.

FIELD

Embodiments described herein relate generally to an X-ray diagnosis apparatus.

BACKGROUND

Conventionally, X-ray diagnosis apparatuses are provided with a road map function as a function to support manipulations during intervention treatments. The road map function supports manipulations of a medical device in a blood vessel, by generating a blood vessel image while using image data acquired with the use of a contrast agent and including information about the blood vessel and further displaying the generated blood vessel image so as to mask a fluoroscopic image.

Further, X-ray diagnosis apparatuses are also provided with a filtering function to control X-ray radiating processes by using various types of filters, for the purpose of reducing radiation exposure amounts of examined a subject during acquisitions of X-ray images. For example, an X-ray diagnosis apparatus uses such a filtering function to exercise control in such a manner that the radiation dose of the X-rays to be radiated onto the region other than a region of interest is arranged to be lower than the radiation dose of the X-rays radiated onto the region of interest including a site to be treat and a medical device, for the purpose of reducing the radiation exposure amount of the subject while generating a sharp X-ray image of the region of interest.

BRIEF DESCRIPTION OF THE DRAWINGS

FIG. 1 is a block diagram illustrating an exemplary configuration of an X-ray diagnosis apparatus according to a first embodiment;

DETAILED DESCRIPTION

Figure 2:
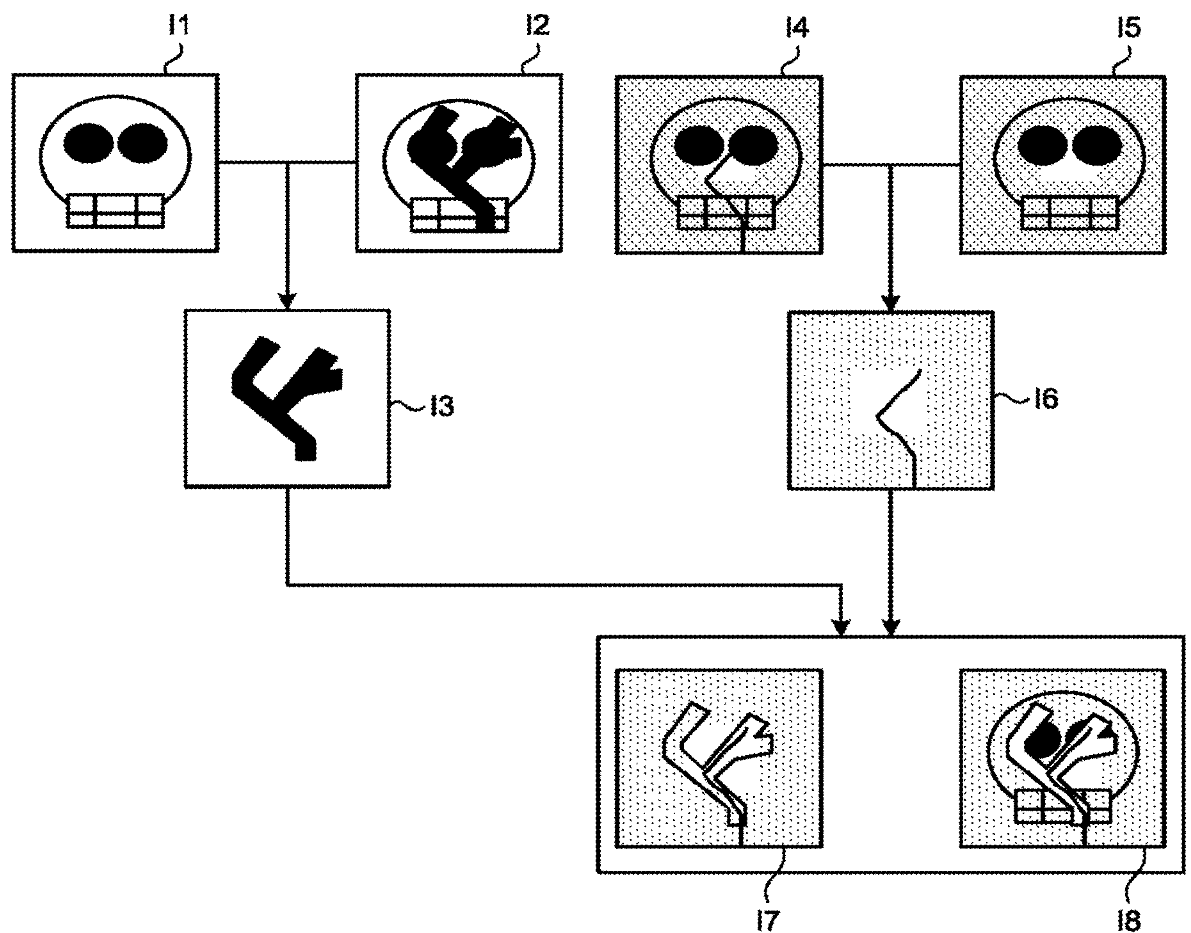
FIG. 2 is a drawing for explaining a fluoroscopy road map according to the first embodiment.

An X-ray diagnosis apparatus according to an embodiment comprises processing circuitry. The processing circuitry is configured to acquire a first X-ray image on a basis of X-rays radiated onto a subject in a first radiation dose. The processing circuitry is configured to acquire a second X-ray image on a basis of X-rays radiated onto the subject in a second radiation dose lower than the first radiation dose. The processing circuitry is configured to acquire a third X-ray image on a basis of X-rays radiated onto a region of interest of the subject into which a medical device is inserted and onto a region other than the region of interest, in mutually-different radiation doses. The processing circuitry is configured to obtain position information of the region of interest in the third X-ray image. And the processing circuitry is configured to obtain positions corresponding to the region of interest in the first X-ray image and in the second X-ray image on a basis of the position information and to generate a subtraction image by calculating a difference between the region of interest in the third X-ray image and a region corresponding to the region of interest in the first X-ray image and calculating a difference between a region other than the region of interest in the third X-ray image and a region corresponding to the region other than the region of interest in the second X-ray image.

Exemplary embodiments of the X-ray diagnosis apparatus will be explained below, with reference to the accompanying drawings. The X-ray diagnosis apparatus of the present disclosure are not limited to the embodiments described below.

First, an exemplary configuration of an X-ray diagnosis apparatus 100 according to a first embodiment will be explained with reference to FIG. 1. FIG. 1 is a block diagram illustrating the exemplary configuration of the X-ray diagnosis apparatus 100 according to the first embodiment. As illustrated in FIG. 1, the X-ray diagnosis apparatus 100 according to the first embodiment includes a high-voltage generator 11, an X-ray tube 12, a collimator 13*a*, a filter 13*b*, a tabletop 14, a C-arm 15, and an X-ray detector 16. Further, the X-ray diagnosis apparatus 100 according to the first embodiment includes a C-arm rotating/moving mechanism 17, a tabletop moving mechanism 18, C-arm/tabletop mechanism controlling circuitry 19, collimator/filter controlling circuitry 20, processing circuitry 1, input circuitry 22, and a display 23. Further, the X-ray diagnosis apparatus 100 according to the first embodiment includes image data generating circuitry 24, storage circuitry 25, and image processing circuitry 26. Also, the X-ray diagnosis apparatus 100 is connected to an injector 30. Furthermore, as illustrated in FIG. 1, in the X-ray diagnosis apparatus 100, the configurations are connected to one another, so that various types of electric signals are transmitted and received among the configurations and so that electric signals are transmitted to and received from the injector 30.

The injector 30 is a device used for injecting a contrast agent through a catheter inserted in a subject P. The injection of the contrast agent from the injector 30 is executed according to an injection instruction received via the processing circuitry 21 (explained later). More specifically, the injector 30 executes the injection of the contrast agent in accordance with contrast agent injection-start and injection-stop instructions received from the processing circuitry 21 (explained later) as well as contrast agent injection conditions including an injection speed and the like. Alternatively, the injector 30 may start and stop the injection according to injection instructions directly input to the injector 30 by the operator.

In the X-ray diagnosis apparatus 100 illustrated in FIG. 1, processing functions thereof are stored in the storage circuitry 25 in the form of computer-executable programs. The C-arm/tabletop mechanism controlling circuitry 19, the collimator/filter controlling circuitry 20, the processing circuitry 21, the image data generating circuitry 24, and the image processing circuitry 26 are processors each configured to realize the function thereof corresponding to a relevant one of the programs, by reading and executing the program from the storage circuitry 25. In other words, each circuitry that has read the corresponding program has the function corresponding to the read program.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors each realize the functions thereof by reading and executing the program stored in the storage circuitry 25. It is also acceptable to directly incorporate the programs into the circuits of the processors, instead of storing the programs in the storage circuitry 25. In that situation, the processors each realize the functions thereof by reading and executing the program incorporated in the circuit thereof. Further, as for the processors according to the first embodiment, each of the processors may be structured as single circuit. Alternatively, it is also acceptable to realize the functions thereof by structuring a single processor by combining together a plurality of independent circuits.

An acquiring function 211 according to the first embodiment an example of an acquiring process performed by the processing circuitry set forth in the claims. An obtaining function 212 according to the first embodiment is an example of an obtaining process performed by the processing circuitry set forth in the claims. A generating function 213 according to the first embodiment is an example of a generating process performed by the processing circuitry set forth in the claims. A display controlling function 214 according to the first embodiment is an example of a display controlling process performed by the processing circuitry set forth in the claims. A filter controlling function 215 according to the first embodiment is an example of a filter controlling process performed by the processing circuitry set forth in the claims.

Under control of the processing circuitry 21, the high-voltage generator 11 is configured to generate a high voltages and to supply the generated high voltage to the X-ray tube 12. The X-ray tube 12 is configured to generate an X-ray by using the high voltage supplied thereto from the high-voltage generator 11. Under control of the collimator/filter controlling circuitry 20, the collimator 13*a* is configured to limit the X-rays generated by the X-ray tube 12 so that the X-rays are selectively radiated onto a region from which an X-ray image is to be acquired. For example, the collimator 13*a* includes four slidable limiting blades. Under the control of the collimator/filter controlling circuitry 20, the collimator 13*a* limits the X-rays generated by the X-ray tube 12 by sliding the limiting blades so that the X-rays are radiated onto the subject P. The limiting blades are each a plate-like member configured by using lead or the like and are provided near an X-ray radiation opening of the X-ray tube 12, so as to be able to regulate the radiation range of the X-rays.

The filter 13*b* is an X-ray filter used for adjusting the X-rays emitted from the X-ray tube 12. For example, for the purpose of reducing the radiation exposure amount of the subject P Arid improving the image quality of image data, the filter 13*b* is configured to reduce soft-ray components that are easily absorbed by the subject P and to reduce high-energy component, that may degrade the contrast of X-ray images, by changing the characteristics of the X-rays passing therethrough with the material and/or the thickness thereof.

Further, the filter 13*b* is configured to attenuate the X-rays radiated from the X-ray tube 12 onto the subject P so as to have a predetermined distribution, by changing the radiation dose and the radiation range of the X-rays with the material, the thickness, and/or the position thereof. For example, the filter 13*b* functions as a Region Of Interest (ROI) filter configured to control the distribution of X-ray radiation doses, so that, within a region of the subject P from which an X-ray image is to be acquired, the region of interest has a higher radiation dose, while the region other than the region of interest has a lower radiation dose. Also, for example, the filter 13*b* functions as an X-ray filter configured to control the distribution of X-ray radiation doses so that the X-ray radiation doses are uniform over the entire area of the region of the subject P from which an X-ray image is to be acquired.

For example, the filter has an opening in a part thereof to pass X-rays without attenuating the X-rays. In other words, the filter 13*b* has a region (which hereinafter may be referred to as a "first region") that attenuates passing X-rays at an attenuation rate corresponding to the material and the thickness thereof, as well as the opening that passes X-rays without attenuating the X-rays. In that situation, the X-rays radiated onto the subject P via the opening has a radiation dose higher than that of the X-rays radiated onto the subject P via the first region.

Alternatively, for example, the filter 13*b* has the first region and another region (which hereinafter may be referred to as a "second region") that attenuates passing X-rays at an attenuation rate lower than the attenuation rate of the X-rays passing through the first region. For example, the second region may be structured so that the thickness in the X-ray radiation direction is smaller than that of the first region. Further, for example, the second region may be structured by using a material having a smaller X-ray absorption coefficient than that of the first region.

In this situation, the filter 13*b* is able to control the distribution of X-ray radiation doses, by moving one selected from between the opening or the second region. Next, a process of controlling the distribution of the X-ray radiation doses performed by the filter 13*b* will be explained. In the following sections, an example will be explained in which either the opening or the second region is moved as a result of moving of the filter 13*b*. Further, in the following sections, an example will be explained in which the filter 13*b* has the opening in a part thereof to pass X-rays without attenuating the X-rays.

For example, under the control of the processing circuitry 21, the filter 13*b* moves in directions to get closer to and away from the X-ray tube 12, as arranged by the collimator/ filter controlling circuitry 20. In other words, the filter 13*b* moves the opening in the directions to get closer to and away from the X-ray tube 12 as a result of the moving of the filter 13*b* itself.

When the X-ray radiation range includes the opening, a part of the X-rays emitted from the X-ray tube 12 is radiated onto the subject P via the opening, and another part of the X-rays is radiated onto the subject P after being attenuated by the filter 13*b*. In that situation, the filter 13*b* functions as a ROI filter configured to control the distribution of X-ray radiation doses in such a manner that, within a region of the subject P from which an X-ray image is to be acquired, the region of interest has a higher radiation dose, while the region other than the region of interest has a lower radiation dose. In this situation, the longer the distance between the opening and the X-ray tube 12 is, the smaller is the region onto which the X-rays in a higher radiation dose are radiated via the opening. In other words, the filter 13*b* is able to control the size of the region of interest, by moving the opening in the directions to get closer to and away from the X-ray tube 12.

Further, under the control of the processing circuitry 21, the filter 13*b* moves in a direction perpendicular to the directions to get closer to and away from the X-ray tube 12, as arranged by the collimator/filter controlling circuitry 20. In this manner, the filter 13*b* is able to control the position of the region of interest. Further, by moving so that the X-ray radiation range does not include the opening, the filter 13*b* exercises control so that all of the X-rays emitted from the X-ray tube 12 are radiated onto the subject P after being attenuated by the filter 13*b*. In that situation, the filter 13*b* functions as an X-ray filter configured to exercise control so that X-rays in a lower radiation dose is radiated over the entire area of the region of the subject P from which an X-ray image is to be acquired. Also, by moving so as not to be included in the X-ray radiation range, the filter 13*b* is able to cause X-rays in a higher radiation dose to be radiated onto the entire area of the region of the subject P from which an X-ray image is to be acquired. The above process of controlling the distribution of the X-ray radiation doses performed by the filter 13*b* can similarly be performed also when the filter 13*b* has the second region instead of the opening.

The tabletop 14 is a bed on which the subject P is placed and is provided on a couch (not illustrated). The subject P is not included in the X-ray diagnosis apparatus 100. The X-ray detector 16 is configured to detect X-rays that have passed through the subject P. For example, the X-ray detector 16 includes detecting elements arranged in a matrix formation. The detecting elements are configured to convert the X-rays that have passed through the subject P into electric signals, to accumulate the electric signals, and to transmit the accumulated electric signals to the image data generating circuitry 24.

The C-arm 15 holds the X-ray tube 12, the collimator 13*a*, the filter 13*b*, and the X-ray detector 16. These elements are positioned by the C-arm 15 in such a manner that X-ray tube 12, the collimator 13*a*, and the filter 13*b* oppose the X-ray detector 16 while the subject P is interposed therebetween. Although FIG. 1 illustrates an example in which the X-ray diagnosis apparatus 100 is a single-plane apparatus, possible embodiments are not limited to this example. The X-ray diagnosis apparatus 100 may be a bi-plane apparatus.

The C-arm rotating/moving mechanism 17 is a mechanism configured to rotate and move the C-arm 15. The tabletop moving mechanism 18 is a mechanism configured to move the tabletop 14. Under the control of the processing circuitry 21, the C-arm/tabletop mechanism controlling circuitry 19 is configured to regulate the rotation and the moving of the C-arm 15 and the moving of the tabletop 14, by controlling the C-arm rotating/moving mechanism 17 and the tabletop moving mechanism 18. Under the control of the processing circuitry 21, the collimator/filter controlling circuitry 20 is configured to control the radiation range of the X-rays radiated onto the subject P, by regulating the opening degree of the limiting blades included in the collimator 13*a*. Further, under the control of the processing circuitry 21, the collimator/filter controlling circuitry 20 is configured to control the distribution of the radiation dose of the X-rays radiated onto the subject P, by regulating the position of the filter 13*b*.

The image data generating circuitry 24 is configured to generate image data by using the electric signals converted from the X-rays by the X-ray detector 16 and to store the generated image data into the storage circuitry 25. For example, the image data generating circuitry 24 generates the image data by applying a current/voltage conversion, an Analog/Digital (A/D) conversion, and/or a parallel/serial conversion to the electric signals received from the X-ray detector 16. In an example, the image data generating circuitry 24 chronologically generates pieces of image data of a fluoroscopic image including the position and the shape of a medical device during a manipulation of an intervention treatment. In another example, the image data generating circuitry 24 generates image data based on X-rays that have passed through the subject P into whom no contrast agent is injected and image data based on X-rays that have passed through the subject P into whom a contrast agent is injected. Further, in yet another example, the image data generating circuitry 24 generates various types of image data used for generating a wire mask image (explained later). After that, the image data generating circuitry 24 stores the generated image data into the storage circuitry 25.

The storage circuitry 25 is configured to receive and store therein the image data generated by the image data generating circuitry 24. For example, the storage circuitry 25 stores therein the image data based on the X-rays that have passed through the subject P into whom no contrast agent is injected and image data based on the X-rays that have passed through the subject P into whom a contrast agent is injected, as well as image data used for generating the wire mask image (explained later). Further, for example, the storage circuitry 25 is also able to store therein all or a part of image data of a fluoroscopic image. Further, the storage circuitry 25 stores therein the programs corresponding to the various types of functions read and executed by the circuitry illustrated in FIG. 1. In an example, the storage circuitry 25 stores therein a program corresponding to the acquiring function 211, a program corresponding to the obtaining function 212, a program corresponding to the generating function 213, and a program corresponding to the display controlling function 214 and the filter controlling function 215 that are read and executed by the processing circuitry 21.

The image processing circuitry 26 is configured to perform various types of image processing processes on the image data stored in the storage circuitry 25. For example, the image processing circuitry 26 generates a subtraction image by performing a subtraction between the image data of a fluoroscopic image based on the X-rays that have passed through the subject P into whom a medical device is inserted and the wire mask image (explained later). Further, for example, the image processing circuitry 26 generates a blood vessel image by reading, from the storage circuitry 25, the image data based on the X-rays that have passed through the subject P before a contrast agent is injected and the image data based on the X-rays that have passed through the subject P after the contrast agent is injected and performing a subtraction on the read pieces of image data.

In this situation, the image processing circuitry 26 is capable of executing a scattered ray correction process on the image data of the fluoroscopic image and on the image data used for generating the wire mask image (explained later). Further, the image processing circuitry 26 is also capable of performing a noise reducing process while using an image processing filter such as a moving average (smoothing) filter, a Gaussian filter, a median filter, or the like. In addition, by using one frame immediately prior to administering a contrast agent as a mask image, the image processing circuitry 26 is capable of keeping at a minimum level mistakes in a position aligning prose (a registration process) caused by body movements. In other words, the image processing circuitry 26 is capable of performing a pre-processing process including a noise removal and a position misalignment correction to each of the acquired X-ray images.

The input circuitry 22 is realized by using a trackball, a switch button, a mouse, a keyboard, and/or the like used for inputting various types of instructions and various types of settings. The input circuitry 22 is connected to the processing circuitry 21 and is configured to convert an input operation received from the operator into an electric signal and outputs the electric signal to the processing circuitry 21. The display 23 is configured to display a Graphical User Interface (GUI) used for receiving an instruction from the operator and any of the various types of X-ray images generated by the image processing circuitry 26. For example, under the control of the processing circuitry 21, the display 23 displays a subtraction image obtained by subtracting background components such as bones from the frames of a fluoroscopic image sequentially generated during a manipulation, as well as various types of X-ray images such as a blood vessel image displayed as being superimposed on (as masking) the subtraction image.

The processing circuitry 21 is configured to control operations of the entirety of the X-ray diagnoses apparatus 100 by executing the acquiring function 211, the obtaining function 212, the generating function 213, the display controlling function 214, and the filter controlling function 215. For example, the processing circuitry 21 performs various types of processes by reading and executing, from the storage circuitry 25, a program for controlling the entirety of the apparatus. For example, the processing circuitry 21 controls the X-ray radiation dose and turning on/off of the X-rays radiated onto the subject P, by controlling the high-voltage generator 11 according to an instruction of the operator transferred thereto from the input circuitry 22 and regulating the voltage supplied to the X-ray tube 12. Further, for example, the processing circuitry 21 regulates the rotation and the moving of the C-arm 15 and the moving of the tabletop 14, by controlling the C-arm/tabletop mechanism controlling circuitry 19 according to an instruction from the operator. Further, for example, the processing circuitry 21 controls the radiation range of the X-rays radiated onto the subject P, by controlling the collimator/filter controlling circuitry 20 and regulating the opening degree of the limiting blades included in the collimator 13*a*, according to an instruction from the operator.

Further, for example, the processing circuitry 21 controls the radiation dose of the X-rays radiated onto the subject P and further controls the X-ray radiation range in correspondence with each of the various X-ray radiation doses, by controlling the collimator/filter controlling circuitry 22 and regulating the position of the filter 13*b* according to an instruction from tie operator, as a result of reading and executing the program corresponding to the filter controlling function 215 from the storage circuitry 25. In other words, the processing circuitry 21 controls the distribution of X-ray radiation dose by controlling the collimator/filter controlling circuitry 20.

Further, the processing circuitry 21 controls the image data generating process performed by the image data generating circuitry 24 and the image processing process performed by the image processing circuitry 26, according to instructions from the operator. Further, the processing circuitry 21 exercises control so that the display 23 displays the GUT used for receiving instructions from the operator, any of the images stored in the storage circuitry 25, and the like. In addition, the processing circuitry 21 controls timing with which the contrast agent is injected, by transmitting signals to start and end the contrast agent injection, to the injector 30. Functions of the processing circuitry 21 will be explained in detail later.

The exemplary configuration of the X-ray diagnosis apparatus 100 has thus been explained. The X-ray diagnosis apparatus 100 according to the first embodiment improves efficiency in intervention treatments with the processes performed by the processing circuitry explained in detail below. More specifically, the X-ray diagnosis apparatus 100 improves efficiency of medical treatments by generating the wire mask image that tracks a movement of a region of interest (ROI) during a fluoroscopy procedure using the ROI filter so as to make it possible to generate the subtraction image rendering only the medical device while keeping the ROI filter in operation. In this situation, the wire mask image is an image required when only the medical device such as a catheter is rendered in relation to the extending of a blood vessel, within a fluoroscopy road map. Further, the X-ray diagnosis apparatus 100 improves the efficiency of medical treatments by making it possible to implement a fluoroscopy road map function by which, while keeping the ROI filter in operation, the subtraction image rendering the medical device is displayed while being masked by a blood vessel image rendering the extending of the blood vessel. In the following sections, processes performed by the X-ray diagnosis apparatus 100 according to the first embodiment will be explained in detail.

First, the fluoroscopy road map function realized by the X-ray diagnosis apparatus 100 while keeping the ROI filter in operation will be explained with reference to FIG. 2. FIG. 2 is a drawing for explaining a fluoroscopy road map according to the first embodiment. First, the X-ray diagnosis apparatus 100 acquires a blood vessel image by using a contrast agent. For example, the acquiring function 211 acquires an X-ray image I1 rendering peripheral tissues (a background) such as bones, while no contrast agent is injected to the subject P. Further, the acquiring function 211 acquires an X-ray image I2 including the position and the shape of the blood vessel while a contrast agent is injected to the subject P. In one example, as a result of the injector 30 injecting the contrast agent at the time of the acquisition of the X-ray image I2, the acquiring function 211 acquires the X-ray image I2 based on the X-rays that have passed through the subject P after the contrast agent is injected. after that, the acquiring function 211 stores the acquired X-ray images I1 and I2 into the storage circuitry 25. In this situation, the acquiring function 211 is also capable of controlling the image processing circuitry 26 so as to apply a scattered ray correction and/or a beam hardening correction to the acquired X-ray images I1 and I2 before storing the images into the storage circuitry 25.

Subsequently, by controlling the image processing circuitry 26, the generating function 213 generates a blood vessel image I3 by using the X-ray image I1 and the X-ray image I2, as illustrated in FIG. 2. For example, the generating function 213 generates the blood vessel image I3 from which background elements are eliminated and in which the blood vessel is emphasized, by reading the X-ray image I1 and the X-ray image I2 from the storage circuitry 25 and calculating a difference between the X-ray image I1 and the X-ray image I2 that were read.

In the following sections, an example will be explained in which the acquiring function 211 acquires the X-ray image I1 and the X-ray image I2 illustrated in FIG. 2 as "acquisition images". The "acquisition images" are images each acquired by using X-rays in a higher radiation dose than the X-rays used for acquiring a "fluoroscopic image". Further, in the following sections, an example will be explained in which the generating function 213 generates the blood vessel image I3 represented by a Digital Subtraction Angiography (DSA) image, by calculating the difference between the X-ray image I1 and the X-ray image I2. In other words, the generating function 213 generates the blood vessel image I3 used in the fluoroscopy road map by using the acquisition images acquired prior to the fluoroscopy procedure.

Next, as illustrated in FIG. 2, the X-ray diagnosis apparatus 100 generates a subtraction image I6 from which background components other than the medical device are eliminated, by calculating a difference between frames of a fluoroscopic image I4 sequentially generated during a manipulation of an intervention treatment and a wire mask image I5. After that, as illustrated in FIG. 2, the generating function 213 generates a superimposed image I7 by superimposing the blood vessel image I3 and the subtraction image I6 on each other. In this situation, the generating function 213 is also capable of generating a superimposed image I7 by superimposing an X-ray image and the subtraction image I6 on each other, the X-ray image being obtained by adjusting the pixel values of the blood vessel image I3 so as to make the medical device overlapped with the blood vessel visually recognizable. Alternatively, as illustrated in FIG. 2, the generating function 213 may generate a superimposed image I8 obtained by superimposing background components of the subject P on the superimposed image I7. In this situation, the generating function 213 may use the X-ray image I1 and the wire mask image I5 illustrated in FIG. 2 as the background components of the subject P in the superimposed image I8. Alternatively, the generating function 213 may use an X-ray image that is not illustrated as the background components of the subject P in the superimposed image I8.

Figure 3:
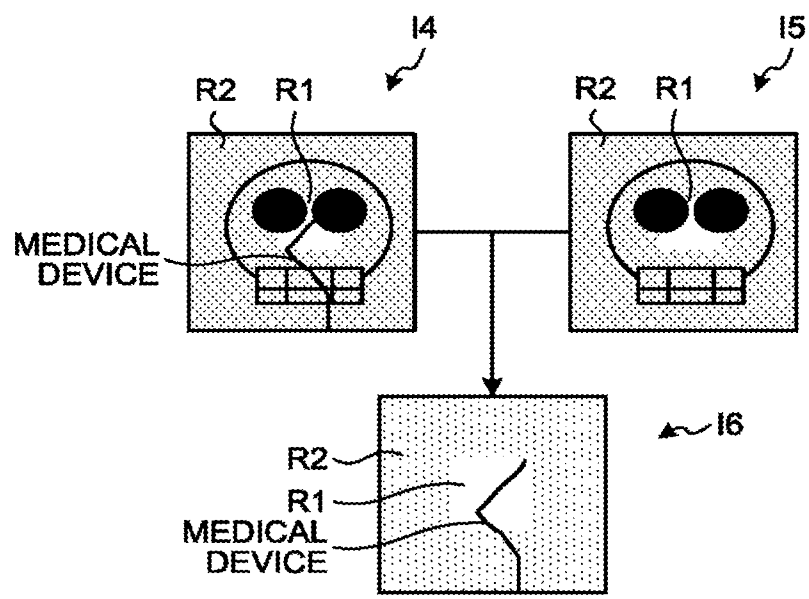
FIG. 3 is a drawing for explaining a fluoroscopic image, a wire mask image, and a subtraction image according to the first embodiment.

Next, the fluoroscopic image I4, the wire mask image I5, and the subtraction image I6 will be explained with reference to FIG. 3. FIG. 3 is a drawing for explaining the fluoroscopic image I4, the wire mask image I5, and the subtraction image I6 according to the first embodiment. FIG. 3 illustrates an example in which a medical treatment is performed by inserting a medical device into a blood vessel in the head of the subject P.

The acquiring function 211 chronologically acquires a plurality of frames of the fluoroscopic image I4 at a predetermined framerate during a manipulation of the intervention treatment. In this situation, as illustrated in FIG. 3, the acquiring function 211 acquires the fluoroscopic image I4 by using the X-rays controlled so as to be radiated onto a region of interest R1 and a region R2 other than the region of interest, in mutually-different radiation doses. More specifically, the filter controlling function 215 controls the position of the filter 13*b* so that the filter 13*b* used for reducing the radiation dose is placed over the region R2. Further, the acquiring function 211 acquires the fluoroscopic image I4 by reducing the radiation dose applied to the region R2 compared to the radiation dose applied to the region of interest R1. After that, the acquiring function 211 controls the image processing circuitry 26 so as to perform a correcting process such as a scattered ray correction on each of the frames of the fluoroscopic image I4 sequentially acquired.

In the following sections, the radiation dose of the X-rays radiated onto the region of interest R1 during the acquisition of the fluoroscopic image I4 may be referred to as a first radiation dose. Also, in the following sections, the radiation dose of the X-rays radiated onto the region R2 other than the region of interest during the acquisition of the fluoroscopic image I4 may be referred to as a second radiation dose. In the present example, the second radiation dose is lower than at least the first radiation dose. For example, the second radiation dose is arranged to be lower than the first radiation dose by causing only the X-rays radiated onto the region R2 to pass through the filter 13*b* and become attenuated. In another example, the second radiation dose is arranged to be lower than the first radiation dose because the X-rays radiated onto the region R2 are attenuated more, due to an arrangement in which the X-rays radiated onto the region R2 pass through a thicker section of the filter 13*b*, whereas the X-rays radiated onto the region of interest R1 pass through a thinner section of the filter 13*b*.

Subsequently, as illustrated in FIG. 3, the generating function 213 generates the subtraction image I6 which is obtained by eliminating the background components other than the medical device from the fluoroscopic image I4 and in which the medical device positioned in the blood vessel is emphasized, by calculating a difference between the fluoroscopic image I4 and the wire mask image I5. In this situation, the wire mask image I5 is at least one frame of X-ray image generated prior to the generation of the fluoroscopic image I4, for the purpose of generating the subtraction image I6.

In this situation, to generate the subtraction image I6 from which the components other than the medical device are eliminated as much as possible, it is desirable to arrange the radiation doses of the X-rays radiated onto the region of interest R1 and onto the region R2 other than the region of interest in the wire mask image I5 to be each equal to the radiation dose of the X-rays used for acquiring the fluoroscopic image I4. Further, it is also desirable to align the position of the region of interest R1 in the wire mask image I5 with the position of the region of interest R1 in the fluoroscopic image I4. In other words, for the purpose of generating the subtraction image I6 which is obtained by eliminating the background components from the fluoroscopic image I4 by a subtraction and from which the components other than the medical device are eliminated as much as possible, it is required that the image quality levels in multiple positions in the images be similar between the fluoroscopic image I4 and the wire mask image I5.

Figure 4:
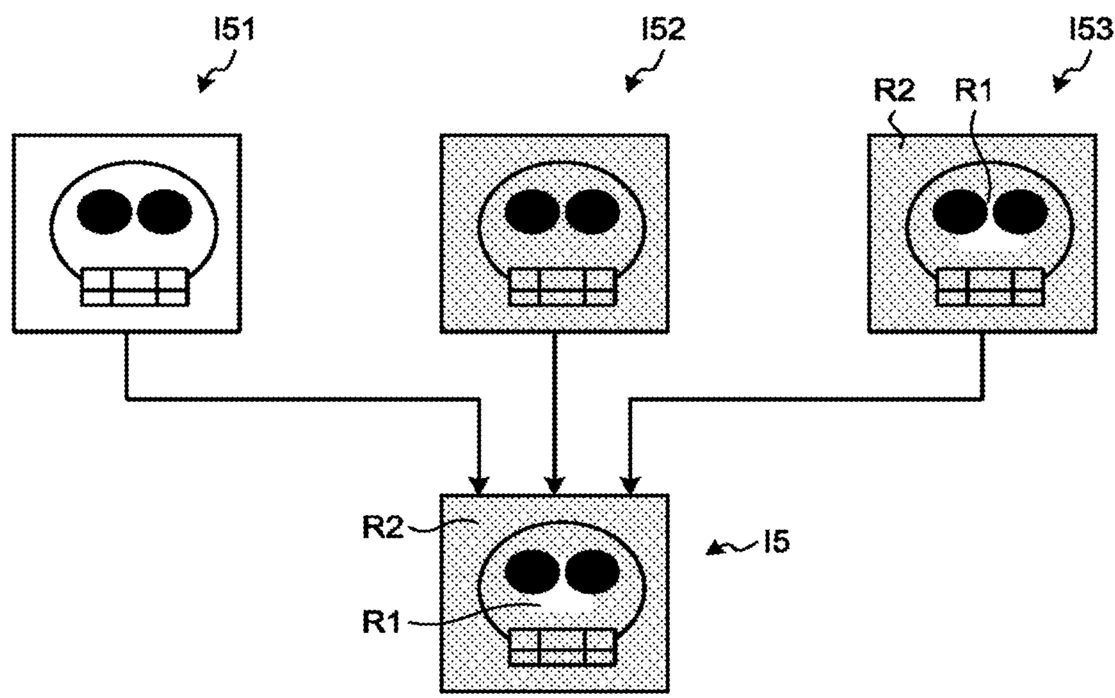
FIG. 4 is a drawing for explaining the wire mask image according to the first embodiment.

Next, a process to acquire the wire mask image I5 will be explained with reference to FIG. 4. FIG. 4 is a drawing for explaining the wire mask image I5 according to the first embodiment. First, on the basis of the X-rays radiated onto the subject P in the first radiation dose, the acquiring function 211 acquiring an X-ray image I51 (which hereinafter may be referred to as a first X-ray image). In other words, the acquiring function 211 acquires the entirety of the X-ray image I51 by using an X-ray condition used for the region of interest R1 in the fluoroscopic image I4. Further, on the basis of the X-rays radiated onto the subject P in the second radiation dose, the acquiring function 211 acquires an X-ray image I52 (which hereinafter may be referred to as a second X-ray image). In other words, the acquiring function 211 acquires the entirety of the X-ray image I52 by using an X-ray condition used for the region R2 other than the region of interest in the fluoroscopic image I4. In the following sections, the fluoroscopic image I4 may be referred to as a third X-ray image.

Further, as illustrated in FIG. 4, the acquiring function 211 acquires an X-ray image I53 on the basis of the X-rays radiated onto the region of interest R1 and the region R2 other than the region of interest in mutually-different radiation doses. In this situation, the acquiring function 211 acquires the X-ray image I53 while ensuring that the position of the region of interest R1 in the X-ray image I53 is the same as the position of the region of interest R1 in the fluoroscopic image I4. For example, the acquiring function 211 acquires the X-ray image I53 while ensuring that the positions of the X-ray tube 12, the collimator 13*a,* the filter 13*b,* and the subject P are the same between the acquisition of the fluoroscopic image I4 and the acquisition of the X-ray image I53.

Further, the obtaining function 212 obtains position information of the region of interest R1 from the X-ray image I53. because the X-ray image I53 described above is an image acquired by radiating the X-rays onto the region of interest R1 and onto the region R2 in the mutually-different radiation doses, the pixel values are significantly different between the region of interest R1 and the region R2. Accordingly, the obtaining function 212 identifies a boundary between the region of interest R1 and the region R2 on the basis of pixel values of the X-ray image I53 and obtains the position information of the region of interest R1 in the X-ray image I53. In this situation, because the position of the region of interest R1 is the same between the X-ray image I53 and the fluoroscopic image I4, it means that the obtaining function 212 obtains the position information of the region of interest R1 in the fluoroscopic image I4. In this situation, the obtaining function 212 obtains the position information every time the position of the region of interest R1 is changed. This feature will be explained later.

In this situation, the acquiring function 211 may acquire the X-ray image I53 by using a radiation dose different from the radiation dose of the X-rays used for acquiring the fluoroscopic image I4. In one example, the acquiring function 211 acquires the X-ray image I53 on the basis of the X-rays radiated onto the region of interest R1 in a radiation dose lower than the first radiation dose and the X-rays radiated onto the region R2 other than the region of interest in a radiation dose lower than the second radiation dose. In other words, as long as the radiation dose is in such a range that the obtaining function 212 is able to obtain the position information of the region of interest R1, the acquiring function 211 may acquire the X-ray image I53 by using X-rays in any radiation dose.

Subsequently, the generating function 213 generates the wire mask image I5 on the basis on the X-ray images illustrated in the top section of FIG. 4. For example, the generating function 213 first obtains positions corresponding to the region of interest R1 in the X-ray image I51 and in the X-ray image I52. Further, the generating function 213 generates the wire mask image I5, on the basis of the information about the positions corresponding to the region of interest R1 in the X-ray image I51 and in the X-ray image I52 as well as the X-ray image I51 and the X-ray image I52. In one example, at first, the generating function 213 extracts a region corresponding to the region of interest R1 from the X-ray image I51. Also, the generating function 213 extracts a region corresponding to the region R2 other than the region of interest, from the X-ray image I52. After that, the generating function 213 is able to generate the wire mask image I5 as illustrated in FIG. 4, by combining together the regions extracted from the X-ray image I51 and from the X-ray image I52.

When the wire mask image I5 has been generated in this manner, the generating function 213 sequentially generates frames of a subtraction image I6 by calculating differences between the plurality of frames of the fluoroscopic image I4 sequentially generated by implementing fluoroscopy and the wire mask image I5. After that, the generating function 213 generates a superimposed image I7 obtained by superimposing the blood vessel image I3 and the subtraction image I6 on each other. Alternatively, the generating function 213 may generate a superimposed image I8 obtained by superimposing the background components of the subject P onto the superimposed image I7.

The display controlling function 214 causes the display 23 to display the superimposed image I7 or the superimposed image I8. For example, the display controlling function 214 supports the manipulations of the medical device in the blood vessel by causing the display 23 to display and to present the operator with the superimposed image I7 or the superimposed image I6 as a moving picture in a real-time manner. Further, the display controlling function 214 may cause the display 23 to display images while switching between the superimposed image I7 and the superimposed image I8, in accordance with a mode switching operation between a fluoroscopic sub-mode to present an X-ray image rendering the blood vessel and the medical device and a landmark mode to present an X-ray image also rendering peripheral tissues in addition to the blood vessel and the medical device.

Figure 5A:
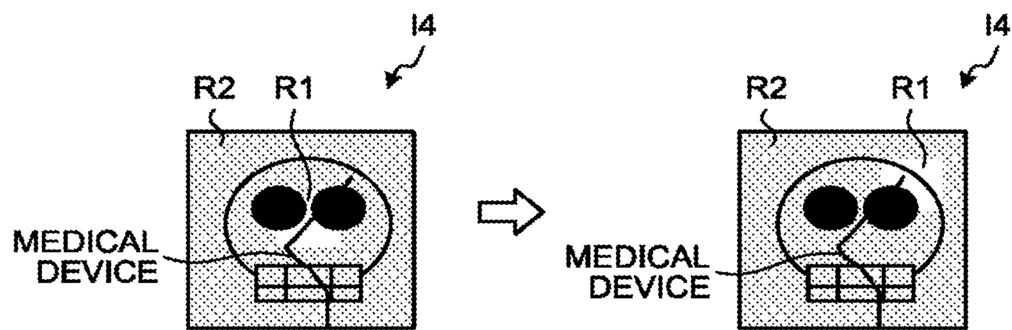
FIG. 5A is a drawing illustrating an example in which the position of a region of interest moves, according to the first embodiment.
Figure 5B:
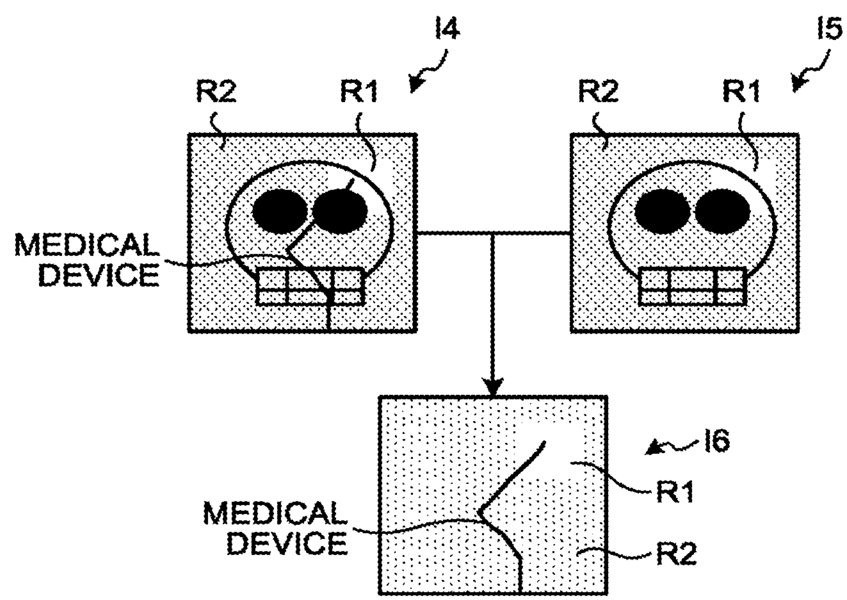
FIG. 5B is a drawing for explaining a wire mask image and a subtraction image in a situation where the position of a region of interest moves, according to the first embodiment.

As explained above, the X-ray diagnosis apparatus 100 according to the first embodiment is configured to generate the wire mask image I5 based on the position of the region of interest R1 and to generate the subtraction image I6 by using the generated wire mask image I5. Further, by using the subtraction image I6 generated in this manner, the X-ray diagnosis apparatus 100 implements the fluoroscopy road map function to display the superimposed image I7 or the superimposed image I8. In this situation, the X-ray diagnosis apparatus 100 implements the fluoroscopy road map function that tracks changes of the positions of the region of interest R1. In the following sections, examples in which the position of the region of interest R1 changes will be explained with reference to FIGS. 5A and 5B. FIG. 5A is a drawing illustrating an example in which the position of the region of interest R1 moves, according to the first embodiment. FIG. 5B is a drawing for explaining the wire mask image I5 and the subtraction image I6 in a situation where the position of the region of interest R1 moves, according to the first embodiment.

For example, while the medical device is being advanced to a treatment target site or when the position of the region of interest R1 is set inappropriately before a manipulation is started, there is a possibility that the tip end of the medical device may go out of the region of interest R1 as indicated in the fluoroscopic image I4 in the left section of FIG. 5A. In this situation, the region R2 other than the region of interest is fluoroscopically acquired by using a radiation dose lower than the radiation dose used for the region of interest R1. Accordingly, because the image of the region R2 is less sharp than the image of the region of interest R1, the efficiency of the manipulation is lowered. In that situation, it is necessary to gradually shift the position of the region of interest R1 in accordance with the movement of the tip end of the medical device. For example, when the position of the region of interest R1 in the fluoroscopic image I4 is to be shifted, the processing circuitry 21 receives an instruction via the input circuitry 22 indicating that the position of the region of interest R1 should be moved. Subsequently, the processing circuitry 21 moves the position of the region of interest R1 as illustrated in the fluoroscopic image I4 in the right section of FIG. 5A, by moving the position of the filter 13*b* in accordance with what is indicated in the instruction.

In this situation, for the purpose of generating, even after the position of the region of interest R1 in the fluoroscopic image I4 has been moved, the subtraction image I6 obtained by subtracting the background components other than the medical device, it is necessary to update the wire mask image I5 in such a manner that the position of the region of interest R1 in the wire mask image I5 is aligned with the post-moving position of the region of interest R1 in the fluoroscopic image I4.

In this situation, the X-ray diagnosis apparatus 100 updates the wire mask image I5 by using the X-ray image I51 and the X-ray image I52 that have already been acquired. At first, the obtaining function 212 obtains the position information of the post-moving region of interest R1 in the fluoroscopic image I4 illustrated in FIG. 513. For example, the obtaining function 212 is able to obtain the position information of the post-moving region of interest R1, on the basis of what is indicated by the instruction received from the operator via the input circuitry 22 indicating that the region of interest R1 be moved.

Subsequently, the generating function 213 generates the wire mask image I5 illustrated in FIG. 5B, on the basis of the information about the positions corresponding to the post-moving region of interest R1 in the X-ray image I51 and in the X-ray image I52, as well as the X-ray image I51 and the X-ray image I52. In one example, the generating function 213 first extracts a region corresponding to the post-moving region of interest R1 from the X-ray image I51. Also, the generating function 213 extracts a region corresponding to the region R2 other than the post-moving region of interest from the X-ray image I52. After that, the generating function 213 is able to generate the wire mask image I5 corresponding to the time after the position of the region of interest R1 has moved, by combining together the regions extracted from the X-ray image I51 and from the X-ray image I52.

After that, as illustrated in FIG. 5B, the generating function 213 generates a subtraction image I6 rendering the medical device, by calculating a difference between the fluoroscopic image I4 corresponding to the time after the position of the region of interest R1 has moved and the updated wire mask image I5. Further, the generating function 213 generates a superimposed image I7 by superimposing the subtraction image I6 based on the updated wire mask image I5 and the blood vessel image I3 on each other. Alternatively, the generating function 213 may generate a superimposed image I8 by superimposing the background components of the subject P on the superimposed image I7. After that, the display controlling function 214 causes the display 23 to display the superimposed image I7 or the superimposed image I8 corresponding to the time after the position of the region of interest R1 has moved.

Figure 6:
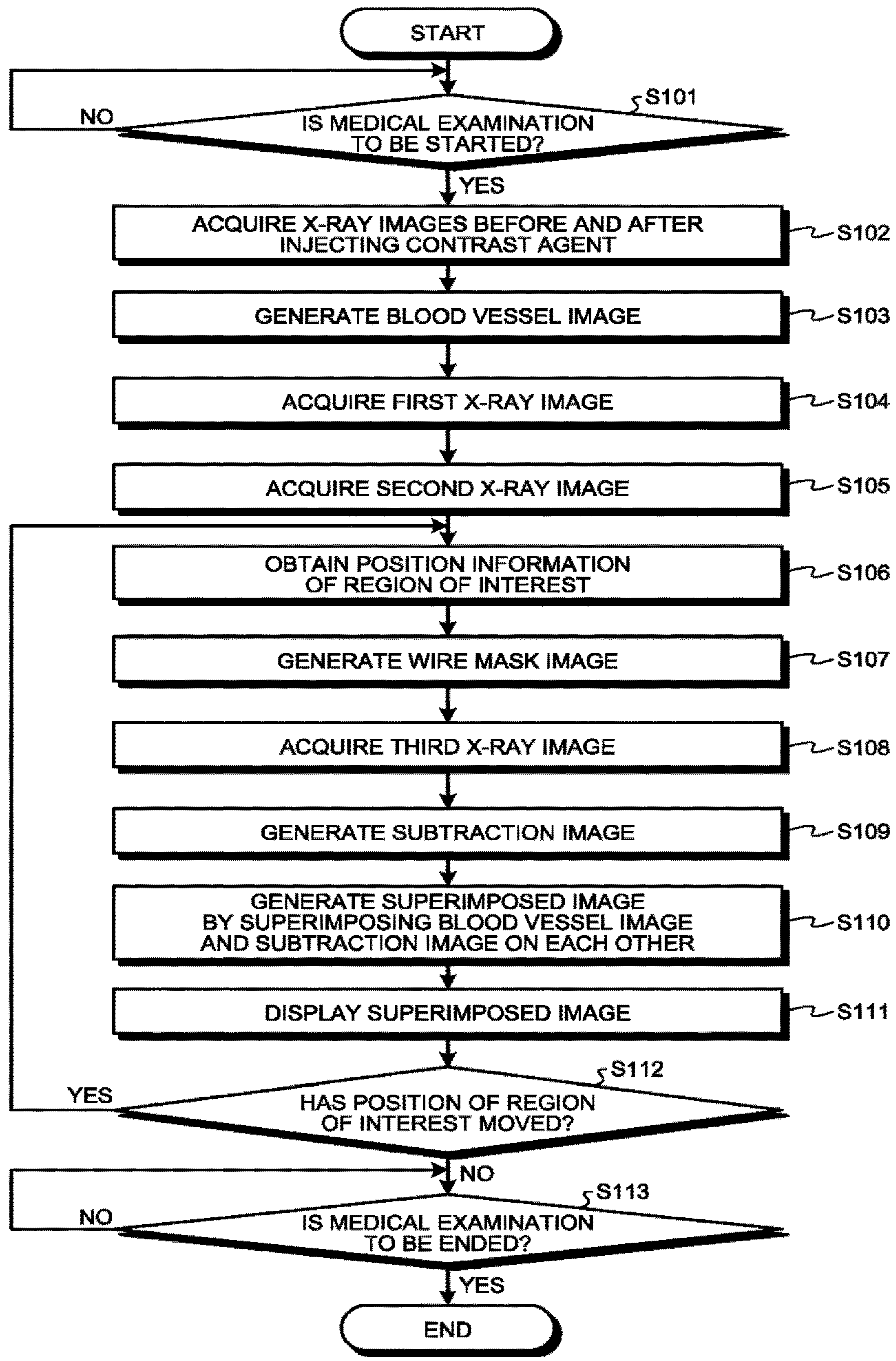
FIG. 6 is a flowchart for explaining a flow of a series of processes performed by the X-ray diagnosis apparatus according to the first embodiment.

Next, an example of a processing procedure performed by the X-ray diagnosis apparatus 100 will be explained, with reference to FIG. 6. FIG. 6 is a flowchart for explaining a flow of a series of processes performed by the X-ray diagnosis apparatus 100 according to the first embodiment. Steps S102, S104, S105, and S108 are steps corresponding to the acquiring function 211. Step S106 is a step corresponding to the obtaining function 212. Steps S103, S107, S109, and S110 are steps corresponding to the generating function 213. Steps S111 is a step corresponding to the display controlling function 214.

First, the processing circuitry 21 judges whether or not a command to start a medical examination has been received (step S101). Unless the starting command is received (step S101: No), the processing circuitry 21 is in a standby state. On the contrary, when the starting command is received (step S101: Yes), the processing circuitry 21 acquires an X-ray image based on X-rays that have passed through the subject P before a contrast agent is injected and an X-ray image based on X-rays that have passed through the subject P after the contrast agent is injected (step S102). Further, the processing circuitry 21 generates a blood vessel image by calculating a difference between the X-ray images before and after the injection of the contrast agent (step S103).

Subsequently, the processing circuitry 21 acquires the first X-ray image by radiating X-rays onto the subject P in the first radiation dose (step S104). Further, the processing circuitry 21 acquires the second X-ray image by radiating X-rays onto the subject P in the second radiation dose (step 105). Further, the processing circuitry 21 obtains the position information of the region of interest R1 from an X-ray image acquired on the basis of the X-rays radiated onto the region of interest R1 and onto the region R2 other than the region of interest, in mutually-different radiation doses (step S106). After that, the processing circuitry 21 generates a wire mask image on the basis of the first X-ray image, the second X-ray image, and the position information of the region of interest R1 (step S107).

When a medical device starts being inserted in a blood vessel, the processing circuitry 21 chronologically acquires frames of the third X-ray image, by controlling the filter 13*b* in such a manner that X-rarer are radiated onto the region of interest R1 in the first radiation dose and X-rays are radiated onto the region R2 other than the region of interest in the second radiation dose (step S108). After that, the processing circuitry 21 chronologically generates frames of a subtraction image by calculating the differences between the frames of the third X-ray image that were chronologically acquired and the wire mask image (step S109). Subsequently, the processing circuitry 21 chronologically generates frames of a superimposed image by superimposing the blood vessel image and the frames of subtraction image on each ether (step S110) and causes the display 23 to display the generated frames of superimposed image (step S111).

In this situation, the processing circuitry 21 judges whether or not the position of the region of interest R1 has moved (step S112). When the position of the region of interest R1 has moved (step S112: Yes), the processing circuitry 21 proceeds to step S106 where the processing circuitry 21 obtains the position information of the post-moving region of interest R1 and updates the wire mask image. On the contrary, when the region of interest R1 has not moved (step S112: No), the processing circuitry 21 judges whether or not a command to end the medical examination has been received (step S113). Unless the ending command is received (step S113: No), the processing circuitry 21 is in a standby state On the contrary, when the ending command is received (step S113: Yes), the processing circuitry 21 ends the process.

As explained above, according to the first embodiment, the acquiring function acquires the first. X-ray image on the basis of the X-rays radiated onto the subject P in the first radiation dose. Further, the acquiring function 211 acquires the second X-ray image on the basis of the X-rays radiated onto the subject P in the second radiation dose lower than the first radiation dose. In addition, the acquiring function 211 acquires the third X-ray image on the basis of the X-rays radiated onto the region of interest R1 of the subject P into which the medical device is inserted in the first radiation dose and radiated onto the region R other than the region of interest in the second radiation dose. Further, the obtaining function 212 obtains the position information of the region of interest R1 in the third X-ray image. In addition, on the basis of the position information of the region of interest R1 in the third X-ray image, the generating function 213 obtains the positions corresponding to the region of interest R1 in the first X-ray image and in the second X-ray image. The generating function 213 generates the subtraction image by calculating the difference between the region of interest R1 in the third X-ray image and the region corresponding to the region of interest R1 in the first X-ray image and calculating the difference between the region R2 in the third X-ray image and the region corresponding to the region R2 in the second X-ray image. Consequently, by bringing the ROI filter into operation during the fluoroscopy procedure, the X-ray diagnosis apparatus 100 according to the first embodiment is able to generate the X-ray image of the medical device from which the background components are eliminated by the subtraction, even when the X-rays are radiated onto the region of interest R1 and the region R2 other than the region of interest in the mutually-different radiation doses. Further, during the fluoroscopy procedure in which the ROI filter is in operation, the X-ray diagnosis apparatus 100 is able to improve the efficiency of the intervention treatment while reducing the radiation exposure amount of the subject P, by presenting the operator with the ray image of the medical device.

Further, according to the first embodiment, the X-ray diagnosis apparatus 100 presents the operator with the superimposed image I7 obtained by superimposing the subtraction image I6 rendering the medical device and the blood vessel image I3 rendering the extending of the blood vessel, on each other. Alternatively, the X-ray diagnosis apparatus 100 presents the operator with the superimposed image I8 obtained by superimposing the background components on the superimposed image I7. Consequently, the X-ray diagnosis apparatus 100 according to the first embodiment is able to improve the efficiency of the intervention treatment by implementing the fluoroscopy road map function by which the operator is presented with the extending of the blood vessel and the position and the shape of the medical device, while having the ROI filter in operation and reducing the radiation exposure amount of the subject P.

Further, the generating function 213 according to the first embodiment generates the wire mask image I5 by combining together the region corresponding to the region of interest R1 in the first X-ray image I51 and the region corresponding to the region R2 other than the region of interest in the second X-ray image I52, by using the position information of the region of interest R1. Accordingly, even when the position of the region of interest R1 moves, the X-ray diagnosis apparatus 100 according to the first embodiment is able to improve the efficiency of the intervention treatment, by easily updating the wire mask image I5 by obtaining the position information of the region of interest R1.

Further, when the position of the region of interest R1 has moved, the generating function 213 according to the first embodiment updates the wire mask image I5 on the basis of the first X-ray image I51 and the second X-ray image I52 that have already been acquired. Accordingly, the X-ray diagnosis apparatus 100 according to the first embodiment does not need to re-acquire an X-ray image for the purpose of updating the wire mask image and is thus able to reduce the radiation exposure amount of the subject P.

In the embodiment above, the example is explained in which the X-ray image I1 and the X-ray image I2 are acquired as the "acquisition images", whereas the blood vessel image I3 is generated as the "DSA image". In a second embodiment, an example will be explained in which the X-ray image I1 and the X-ray image I2 are acquired as "fluoroscopic images". In other words, in the second embodiment, the example will be explained in which the X-ray image I1 and the X-ray image I2 are acquired as "fluoroscopic images" that use X-rays in a radiation dose lower than the radiation dose used for acquiring the "acquisition images", similarly to the fluoroscopic image I4.

The X-ray diagnosis apparatus 100 according to the second embodiment has a similar configuration to that of the X-ray diagnosis apparatus 100 according to the first embodiment illustrated in FIG. 1. Parts of the processes performed by the acquiring function 211 and the generating function 213 are different. Accordingly, some of the configurations that are the same as those explained in the first embodiment will be referred to by using the same reference characters as those in FIG. 1, and explanations thereof will be omitted.

Figure 7:
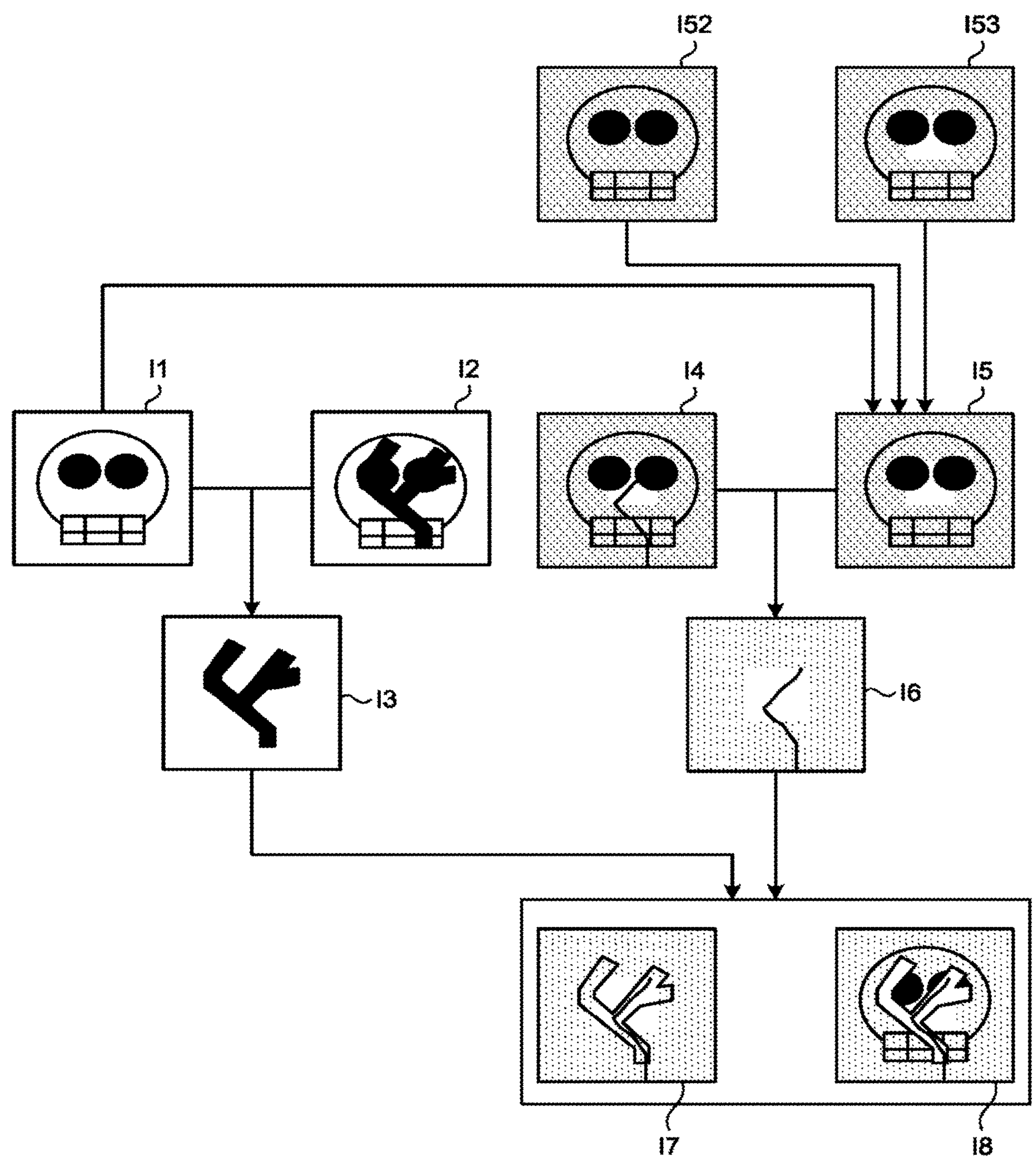
FIG. 7 is a drawing for explaining a fluoroscopy road map according to a second embodiment.

Next, a fluoroscopy road map function according to the second embodiment will be explained, with reference to FIG. FIG. 7 is a drawing for explaining the fluoroscopy road map function according to the second embodiment. First, the acquiring function 211 according to the second embodiment acquires, as illustrated in FIG. 7, the X-ray image I1 based on the X-rays that have passed through the subject P before a contrast agent is injected and the X-ray image I2 based on the X-rays that have passed through the subject P after the contrast agent is injected.

In this situation, for example, the acquiring function 211 acquires the X-ray image I1 and the X-ray image I2 by using the X-rays in the first radiation dose. In other words, the acquiring function 211 acquires the entire areas of the X-ray image I1 and the X-ray image I2, by using the same X-ray condition as the X-ray condition used for the region of interest R1 in the fluoroscopic image I4. After that, as illustrated in FIG. 7, the generating function 213 generates the blood vessel I3 from which the background components such as bones are eliminated, by calculating a difference between the X-ray image I1 and the X-ray image I2.

Further, as illustrated in FIG. 7, the generating function 213 according to the second embodiment generates the wire mask image I5, by using the X-ray image I1 based on the X-rays that have passed through the subject P before the contrast agent is injected and the X-ray image I52 based on the X-rays radiated onto the subject P in the second radiation dose. In one example, at first, the obtaining function 212 obtains the position information of the region of interest R1 in the fluoroscopic image I4, on the basis of the X-ray image I53. Subsequently, the generating function 213 extracts a region corresponding to the region of interest R1 in the X-ray image I1, on the basis of the position information of the region of interest R1. Further, the generating function 213 extracts a region corresponding to the region R2 other than the region of interest from the X-ray image I52, on the basis of the position information of the region of interest R1. After that, by combining together the regions extract the X-ray image I1 and from the X-ray image I52, the generating function 213 is able to generate the wire mask image I5, as illustrated in FIG. 7.

After that, as illustrated in FIG. 7, the generating function 213 generates a subtraction image I6 by calculating a difference between the fluoroscopic image I4 and the wire mask image I5. Further, as illustrated in FIG. 7, the generating function 213 generates a superimposed image by superimposing the blood vessel image I3 and the subtraction image I6 on each other. Alternatively, the generating function 213 may generate a superimposed image I8 by superimposing the background components of the subject P on the superimposed image I7. Further, the display controlling function 214 causes the display 23 to display the superimposed image I7 or the superimposed image I8.

Figure 8:
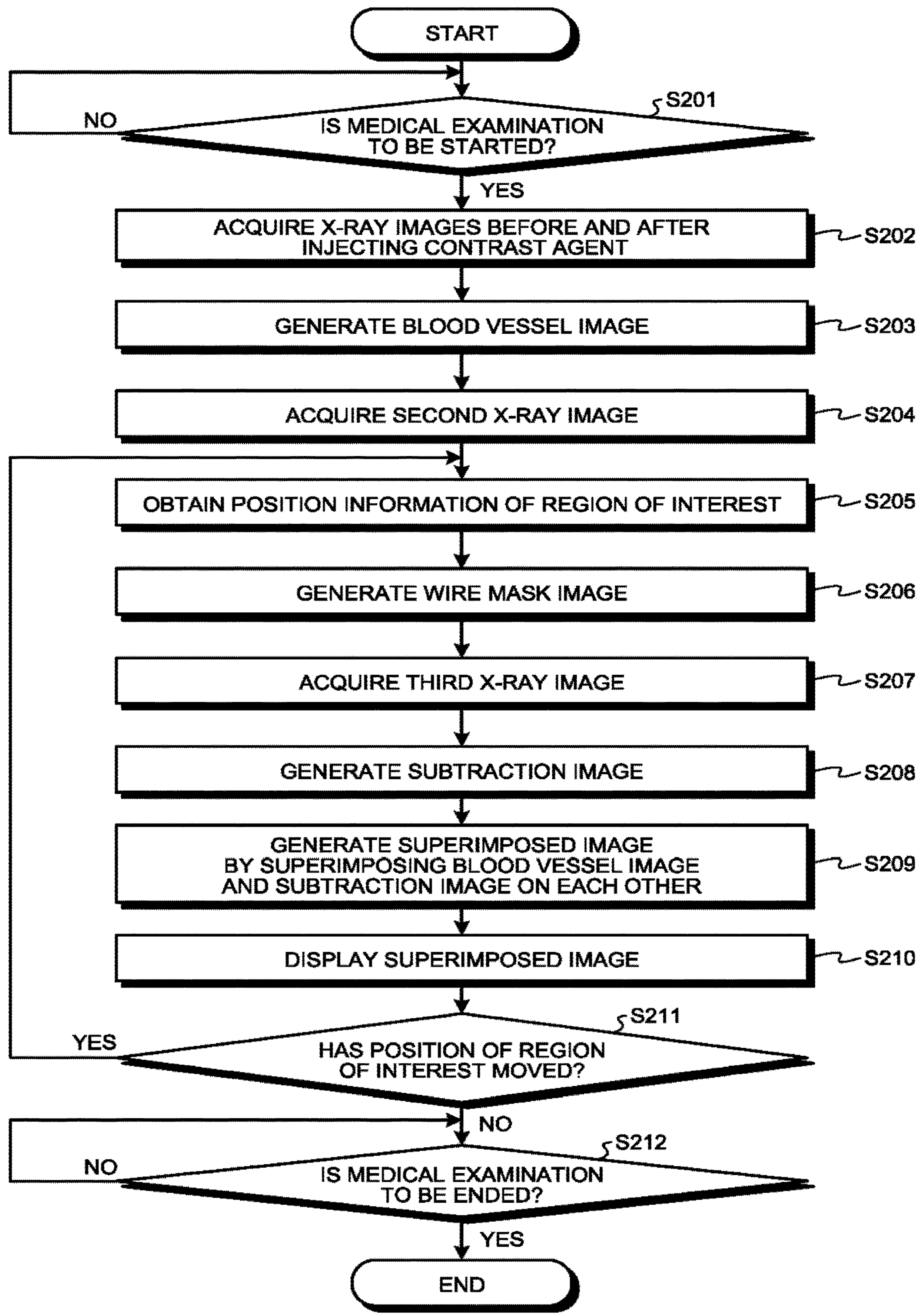
FIG. 8 is a flowchart for explaining a flow of a series of processes performed by an X-ray diagnosis apparatus according to the second embodiment.

Next, an example of a processing procedure performed by the X-ray diagnosis apparatus 100 will be explained, with reference to FIG. 8. FIG. 8 is a flowchart for explaining a flow of a series of processes performed by the X-ray diagnosis apparatus 100 according to the second embodiment. Steps S202, S204, and S207 are steps corresponding to the acquiring function 211. Step S205 is a step corresponding to the obtaining function 212. Steps S203, S206, S208, and S209 are steps corresponding to the generating function 213. Step S210 is a step corresponding to the display controlling function 214.

First, the processing circuitry 21 judges whether or not a command to start a medical examination has been received (step S201). Unless the starting command is received (step S201: No), the processing circuitry 21 is in a standby state. On the contrary, when the starting command is received (step S201: Yes), the processing circuitry 21 acquires an X-ray image based on X-rays that have passed through the subject P before a contrast agent is injected and an X-ray image based on X-rays that have passed through the subject P after the contrast agent is injected, by using X-rays in the first radiation dose ep S202). Further, the processing circuitry 21 generates a blood vessel image by calculating a difference between the X-ray images before and after the injection of the contrast agent (step S203).

Subsequently, the processing circuitry 21 acquires the second X-ray image by radiating X-rays onto the subject P in the second radiation dose (step S204). Further, the processing circuitry 21 obtains the position information of the region of interest R1 from an X-ray image acquired on the basis of the X-rays radiated on the region of interest R1 and the region R2 other than the region of interest, in mutually-different radiation doses (step S205). Further, the processing circuitry 21 generates a wire mask image on the basis of the first X-ray image, the second X-ray image, and the position information of the region of interest R1 (step S206).

When a medical device starts being inserted into a blood vessel, the processing circuitry 21 chronologically acquires frames of the third X-ray image, by controlling the filter 13*b* in such a manner that X-rays are radiated onto the region of interest R1 in the first radiation dose and X-rays are radiated onto the region R2 other than the region of interest in the second radiation dose (step S207). After that, the processing circuitry 21 chronologically generates frames of a subtraction image by calculating the differences between the frames of the third X-ray image that were chronologically acquired and the wire mask image (step S208). Subsequently, the processing circuitry 21 chronologically generates frames of a superimposed image by superimposing the blood vessel image and the subtraction image on each other (step S209) and causes the display 23 to display the generated superimposed image (step S210).

In this situation, the processing circuitry 21 judges whether or not the position of the region of interest R1 has moved (step S211). When the position of the region of interest R1 has moved (step S211: Yes), the processing circuitry 21 proceeds to step S205 where the processing circuitry 21 obtains the position information of the post-moving region of interest R1 and updates the wire mask image. On the contrary, when the position of the region of interest R1 has not moved (step S211: No), the processing circuitry 21 judges whether or not a command to end the medical examination has been received (step S212). Unless the ending command is received (step S212: No), the processing circuitry 21 is in a standby state. On the contrary, when the ending command is received (step S212: Yes), the processing circuitry 21 ends the process.

As explained above, according to the second embodiment, the acquiring function 211 acquires the X-ray image I1 that is the fluoroscopic image based on the X-rays that have passed through the subject P before the contrast agent is injected and the X-ray image I2 that is the fluoroscopic image based on the X-rays that have passed through the subject P after the contrast agent is injected, by using the X-rays in the first radiation dose. In addition, the generating function 213 generates the wire mask image I5 by using, as the first X-ray image, the X-ray image I1 based on the X-rays that have passed through the subject P before the contrast agent is injected. Consequently, the X-ray diagnosis apparatus 100 according to the second embodiment is able to reduce the number of X-ray images acquired for the purpose of generating the wire mask image I5 and is thus able to reduce the radiation exposure amount of the subject P and to shorten the period of time required by the acquisition of the wire mask image.

The first and the second embodiments have thus been explained. It is possible to carry out the present disclosure in various different modes other than those described in the first and the second embodiments.

In the embodiments described above, the example is explained in which the position information of the region of interest R1 in the fluoroscopic image I1 is obtained from the X-ray image I53 acquired on the basis of the X-rays radiated onto the region of interest R1 and the region R2 other than the region of interest in the mutually-different radiation doses In this regard, the position information of the region of interest R1 in the fluoroscopic image I4 may be obtained by using various methods. In the following sections, examples of the process of obtaining the position information of the region of interest R1 performed by the obtaining function 212 will be explained.

Figure 9:
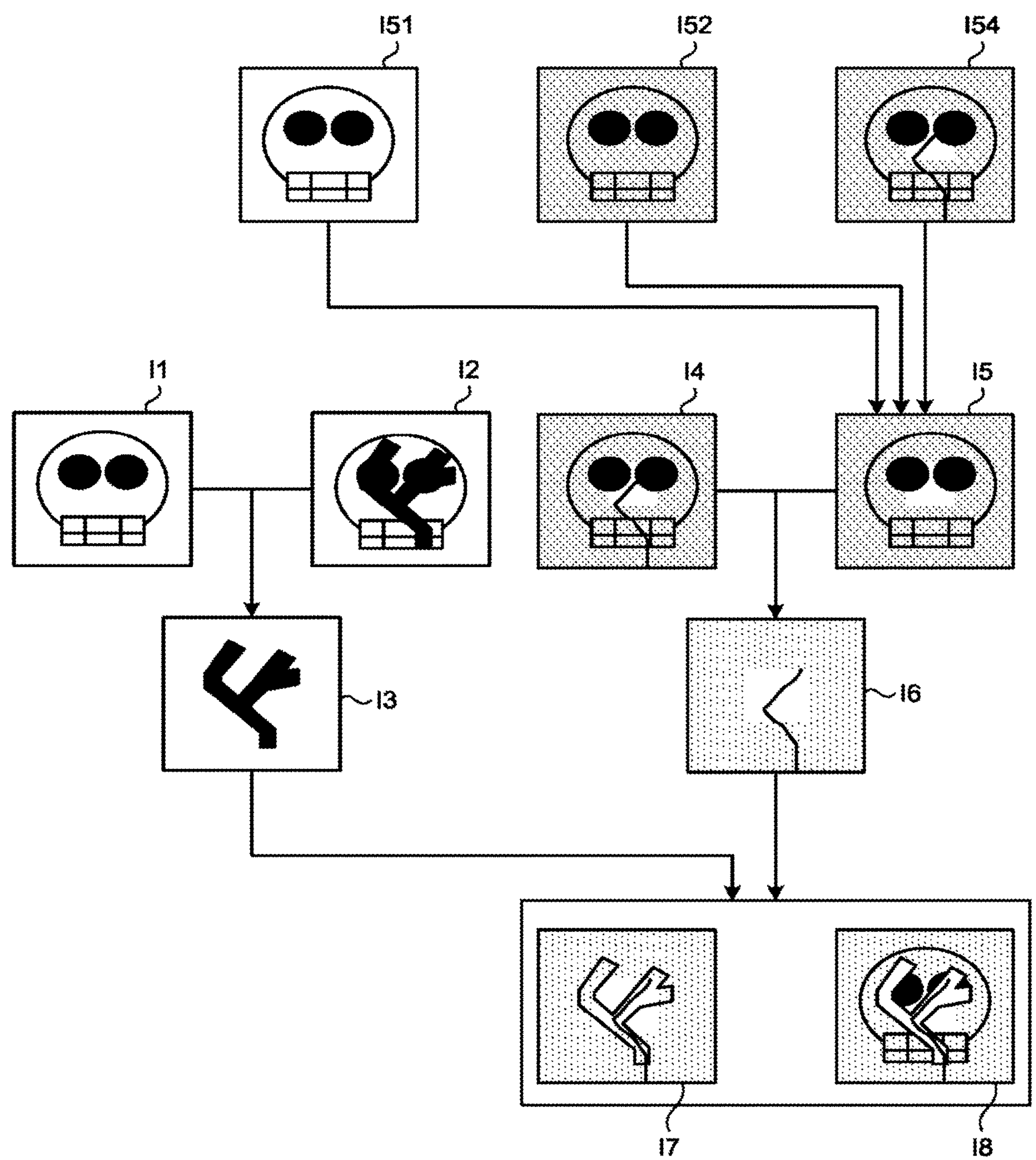
FIG. 9 is a drawing for explaining a fluoroscopy road map according to a third embodiment.

First, an example of the process of obtaining the position information of the region of interest R1 performed by the obtaining function 212 will be explained, with reference to FIG. 9. FIG. 9 is a drawing for explaining a fluoroscopy road map according to a third embodiment. As illustrated in FIG. 9, the acquiring function 211 acquires an X-ray image I54 on the basis of X-rays radiated onto the region of interest R1 and the region R2 other than the region of interest in mutually-different radiation doses, while a medical device is inserted in the subject P. Further, the obtaining function 212 is able to obtain the position information of the region of interest R1 in the fluoroscopic image I4, on the basis of the differences in the pixel value between the region of interest R1 and the region R2 in the X-ray image I54. In other words, the obtaining function 212 is able to obtain the position information of the region of interest R1 even when the medical device is included in the X-ray image I54.

Further, the obtaining function 212 according to the third embodiment is also able to use the fluoroscopic image I4 as the X-ray image I54 illustrated in FIG. 9. In other words, the obtaining function 212 is able to obtain the position information of the region of interest R1 in the fluoroscopic image I4 on the basis of the differences in pixel value between the region gf interest R1 and the region R2 other than the region of interest in the fluoroscopic image I4. In one example, the obtaining function 212 is able to obtain the position information of the region of interest R1 on the basis of a predetermined image frame (e.g., the image frame acquired first) among the plurality of frames of the fluoroscopic image I4 generated chronologically. Further, in another example, the obtaining function 212 is also able to chronologically obtain pieces of position information of the region of interest R1, by using each of the plurality of frames of the fluoroscopic image I4 generated chronologically.

Further, for example, the obtaining function 212 according to the third embodiment is able to obtain the position information of the region of interest R1 in the fluoroscopic image I4, on the basis of the radiation dose and the radiation range of the X-rays radiated onto the subject P. In one example, the obtaining function 212 calculates the radiation range of the X-rays radiated onto the subject P, by using information about the opening degree of the limiting blades in the collimator 13*a* controlled by the processing circuitry 21 and information about the positions of the X-ray tube 12, the collimator 13*a*, the tabletop 14, and the subject P. Further, the obtaining function 212 calculates the radiation dose of the X-rays radiated onto various positions of the subject P, by using information about the position of the filter 13*b* controlled by the processing circuitry 21. After that, on the basis of the radiation dose and the radiation range of the X-rays that were calculated, the obtaining function 212 is able to obtain the position information of the region of interest R1 in the fluoroscopic image I4. In other words, the obtaining function 212 is able to obtain the position information of the region of interest R1, on the basis of a distribution of the X-ray radiation doses for the subject P.

Further, for example, the obtaining function 212 is able to obtain the position information of the region of interest R1, on the basis of the position of one selected from between the opening or the second region of the filter 13*b*. In one example, the obtaining function 212 is able to obtain the position information of the region of interest R1, by identifying, as a contour of the region of interest R1, a set of intersecting points between a plurality of straight lines that pass the X-ray focal point of the X-ray tube 12 and the edge of either the opening or the second region of the filter 13*b* and the detecting surface of the X-ray detector 16.

When it is possible to use a virtual collimator for acquiring the fluoroscopic image I4, the obtaining function 212 is able to obtain the position information of the region of interest R1 in the fluoroscopic image I4 on the basis of information about the virtual collimator. In this situation, the virtual collimator is a function that aids the process of setting an X-ray radiation range by having the position of the collimator 13*a* displayed within a Last Image Hold (LIH) image acquired through a fluoroscopy process.

Figure 10:
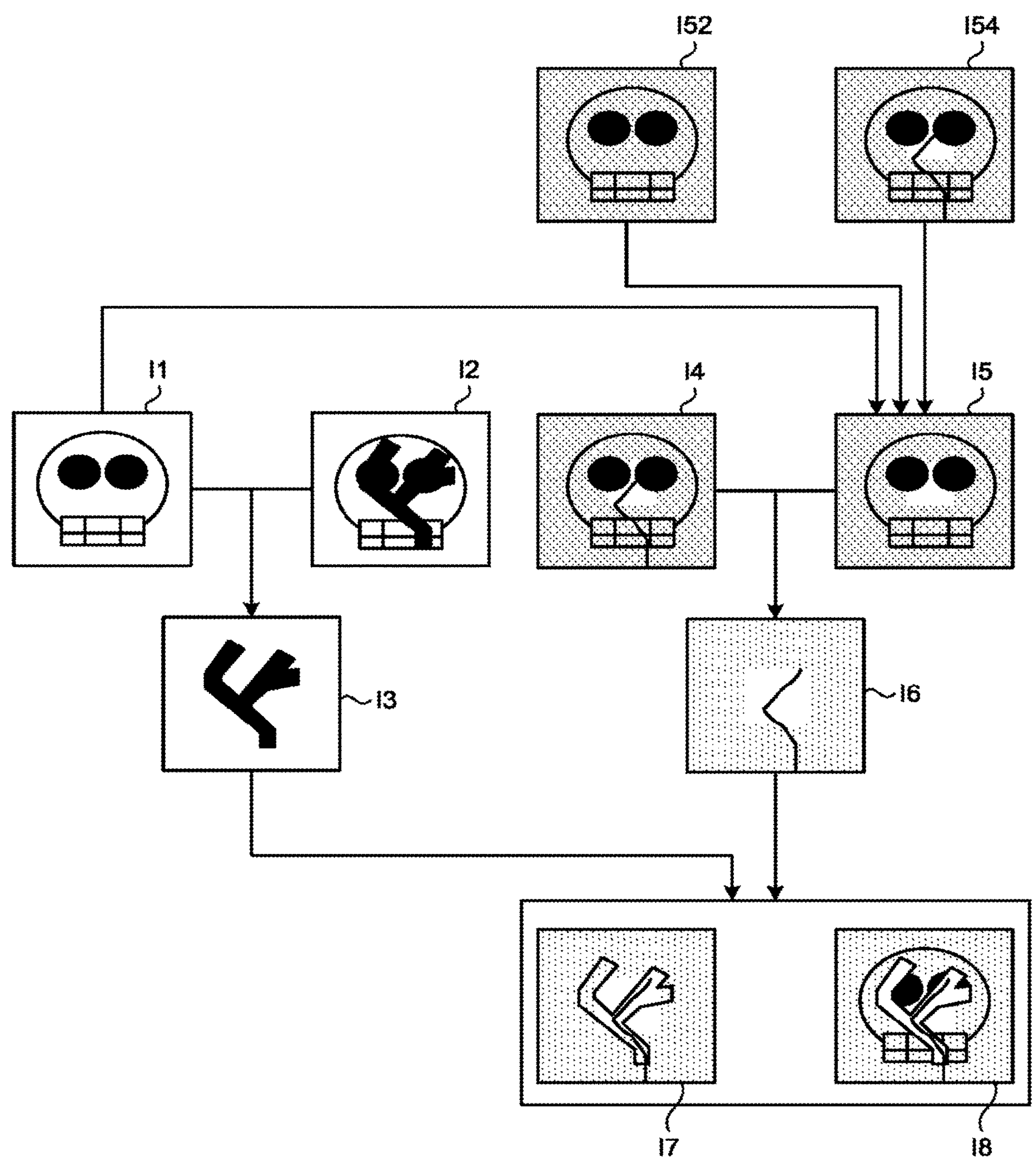
FIG. 10 is a drawing for explaining another fluoroscopy road map according to the third embodiment.

Further, the generating function 213 is able to generate the wire mask image I5 on the basis of any of various combinations of X-ray images. Next, an example of the process of generating the wire mask image I5 will be explained, with reference to FIG. 10. FIG. 10 is a drawing for explaining a fluoroscopy road map according to the third embodiment. For example, as illustrated in FIG. 10, the generating function 213 is able to generate a wire mask image I5, by using the X-ray image I1 that is the fluoroscopic image based on the X-rays that have passed through the subject P before the contrast agent is injected, the X-ray image I52 based on the X-rays radiated onto the subject P in the second radiation dose, and the X-ray image I54 acquired while the medical device is inserted in the subject P.

In the embodiments described above, the example is explained in which the display 23 displays either the superimposed image I7 rendering the blood vessel and the medical device or the superimposed image I8 rendering the peripheral tissues in addition to the blood vessel and the medical device. However, possible embodiments are not limited to this example. For instance, the display controlling function 214 is also able to cause the display 23 to display the subtraction image I6 rendering the medical device.

Further, in the embodiments described above, the example is explained in which the wire mask image I5 is generated, and the subtraction image I6 is further generated by calculating the difference between the fluoroscopic image I4 and the wire mask image I5. However, possible embodiments are not limited to this example. For instance, it is acceptable to omit the process of generating the wire mask image I5 realized by combining the region corresponding to the region of interest R1 within the X-ray image I51, with the region corresponding to the region R2 other than the region of interest within the X-ray image I52. In other words, the wire mask image I5 is an example used for generating the subtraction image I6. Accordingly, it is acceptable to generate the subtraction image I6 without generating the wire mask image I5, by simply calculating the difference between the region of interest R1 in the fluoroscopic image I4 and the region corresponding to the region of interest R1 in the X-ray image I51 and further calculating the difference between the region R2 in the fluoroscopic image I4 and the region corresponding to the region R2 in the X-ray image I52.

Further, in the embodiments described above, the example is explained in which the first X-ray image I51 is acquired by using the X-rays in the first radiation dose, the second X-ray image I52 is acquired by using the X-rays in the second radiation dose, and the fluoroscopic image I4 is acquired by using the X-rays in the first radiation dose and the second radiation dose. However, possible embodiments are not limited to this example. For instance, when the first X-ray image I51 has been acquired by using the X-rays in the first radiation dose, the radiation dose of the X-rays radiated onto the region of interest R1 in the fluoroscopic image I4 may be a radiation dose different from the first radiation dose. Further, for example, when the second X-ray image I52 has been acquired by using the X-rays in the second radiation dose, the radiation dose of the X-rays radiated onto the region R2 other than the region of interest in the fluoroscopic image I4 may be a radiation dose different from the second radiation dose. In other words, it is sufficient when the fluoroscopic image I4 is an X-ray image acquired on the basis of X-rays radiated onto the region of interest R1 and the region R2 in mutually-different radiation doses.

Next, an example will be explained in which the fluoroscopic image I4 is not an X-ray image acquired on the basis of X-rays radiated onto the region of interest. R1 in the first radiation dose and onto the region R2 in the second radiation dose. In the following sections, an example will be explained in which the first X-ray image I51 is acquired by using the X-rays in the first radiation dose, the second X-ray image I52 is acquired by using the X-rays in the second radiation dose, and the fluoroscopic image I4 is acquired on the basis of X-rays radiated onto the region of interest R1 in a third radiation dose and onto the region R2 in a fourth radiation dose. In this situation, the third radiation dose is different from the first radiation dose. The fourth radiation dose is different from the second radiation dose and is lower than the third radiation dose.

First, the acquiring function 211 acquires the X-ray image I51 based on the X-rays radiated onto the subject P in the first radiation dose and the X-ray image I52 based on the X-rays radiated onto the subject P in the second radiation dose. Subsequently, the acquiring function 211 chronologically acquires frames of fluoroscopic image I4 based on the X-rays radiated onto the subject P in the third radiation dose and the fourth radiation dose. After that, the obtaining function 212 obtains the position information of the region of interest R1 in the fluoroscopic image I4. Subsequently, on the basis of the position information of the region of interest R1, the generating function 213 generates a subtraction image I6 by calculating the difference between the X-ray images I51 and I52 and the fluoroscopic image I4.

In this situation, because the first radiation dose is different from the third radiation dose, the X-ray image I51 has a brightness level different from that of the region of interest R1 in the fluoroscopic image I4. Consequently, even when the difference is calculated between the region of interest R1 in the fluoroscopic image I4 and the region corresponding to the region of interest R1 in the X-ray image I51, it may not be possible to subtract and eliminate the background components such as bones. Similarly, even when the difference is calculated between the region R2 other than the region of interest in the fluoroscopic image I4 and the region corresponding to the region R2 in the X-ray image I52, it may not be possible to subtract and eliminate the background components such as bones.

To cope with this situation, the generating function 213 adjusts the gains of the X-rays image I51 and the X-ray image I52 prior to the calculation of the difference between the fluoroscopic image I4 and the X-ray images I51 and I52. More specifically, the generating function 213 increases or decreases, by a certain ratio, the pixel values of the pixels in the region corresponding to the region of interest R1 in the X-ray image I51 in such a manner that an average of the pixel values of the pixels in the region of interest R1 in the fluoroscopic image I4 is equal to an average of the pixel values of the pixels in the region corresponding to the region of interest R1 in the X-ray image I51. In this situation, the generating function 213 may increase or decrease the pixel values of the pixels in the region corresponding to the region R2 in the X-ray image I51 by using a ratio equal to the ratio used for increasing or decreasing the pixel values of the pixels in the region corresponding to the region of interest R1. Further, when the region of interest R1 in the fluoroscopic image I4 includes the medical device, the generating function 213 may use an average of the pixel values of the pixels remaining after excluding the pixels corresponding to the medical device from the region of interest R1, as an average of the pixel values of the pixels in the region of interest R1.

Further, the generating function 213 increases or decreases, by a certain ratio, the pixel values of the pixels in the region corresponding to the region R2 in the X-ray image I52 in such a manner that an average of the pixel values of the pixels in the region R2 in the fluoroscopic image I4 is equal to an average of the pixel values of the pixels in the region corresponding to the region R2 in the X-ray image I52. In this situation, the generating function 213 may increase or decrease the pixel values of the pixels in the region corresponding to the region of interest R1 in the X-ray image I52 by using a ratio equal to the ratio used for increasing or decreasing the pixel values of the pixels in the region corresponding to the region. R2. Further, when the region R2 in the fluoroscopic image I4 includes the medical device, the generating function 213 may use an average of the pixel values of the pixels remaining after excluding the pixels corresponding to the medical device from the region R2, as an average of the pixel values of the pixels in the region R2.

Further, the generating function 213 generates a subtraction image I6 by calculating a difference between the region of interest R1 in the fluoroscopic image I4 and the region corresponding to the region of interest R1 in the X-ray image I51 of which the pixel values have been adjusted and further calculating a difference between the region R2 other than the region of interest in the fluoroscopic image I4 and the region corresponding to the region R2 in the X-ray image I52 of which the pixel values have been adjusted.

In the embodiments described above, the example is explained in which the subtraction image I6 is generated by acquiring the X-ray image I51 based on the X-rays radiated onto the subject P in the first radiation dose and the X-ray image I52 based on the X-rays radiated onto the subject P in the second radiation dose and further calculating the difference between the X-ray images I51 and I52 and the fluoroscopic image I4. In other words, in the embodiments described above, at least two X-ray images used for calculating the difference from the fluoroscopic image I4 are acquired. However, possible embodiments are not limited to this example. In the following sections, an example will be explained in which only one X-ray image is acquired to be used for calculating a difference from the fluoroscopic image I4.

First, the acquiring function 211 acquires an X-ray image (hereinafter, an "X-ray image I9") on the basis of X-rays radiated onto the subject P. In this situation, the acquiring function 211 may acquire the X-ray image I9 by using X-rays in an arbitrary radiation dose. In the following sections, an example will be explained in which the acquiring function 211 has acquired the X-ray image I9 by using X-rays in the first radiation dose.

Subsequently, the acquiring function 211 chronologically acquires frames of fluoroscopic image I4 on the basis of X-rays radiated onto the region of interest R1 and onto the region R2 in mutually-different radiation doses. In this situation, the acquiring function 211 may acquire the fluoroscopic image I4 by using X-rays in an arbitrary radiation dose. In the following sections, an example will be explained in which e acquiring function 211 acquires the fluoroscopic image I4 on the basis of X-rays radiated onto the region of interest R1 in the third radiation dose and onto the region R2 in the fourth radiation dose.

After that, the generating function 213 generates an X-ray image to be used for calculating the difference from the fluoroscopic image I4 by using the X-ray image I9, on the basis of the position information of the region of interest R1 obtained by the obtaining function 212.

For example, from the X-ray image I9, the generating function 213 generates an X-ray image I10 corresponding to the brightness level of the region of interest R1 in the fluoroscopic image I4 and an X-ray image I11 corresponding to the brightness level of the region R2 in the fluoroscopic image I4, as X-ray images to be used for calculating the difference from the fluoroscopic image I4.

In one example, the generating function 213, at first, obtains an average (hereinafter, an "average A1") of the pixel values of the pixels included in the region of interest R1 and an average (hereinafter, an "average A2") of the pixel values of the pixels included in the region R2, on the basis of the position information of the region of interest R1 in the fluoroscopic image I4. Subsequently, the generating function 213 obtains an average (hereinafter, an "average A3") of the pixel values of the pixels included in the region corresponding to the region of interest R1 in the X-ray image I9 and further calculates a ratio of the average A1 to the average A3. The generating function 213 further generates the X-ray image I10 corresponding to the brightness level of the region of interest R1 in the fluoroscopic image I4, by multiplying the pixel values of the pixels in the X-ray image I9 by the calculated ratio. Further, the generating function 213 obtains an average (hereinafter, an "average A4") of the pixel values of the pixels included in the region corresponding to the region R2 in the X-ray image I9 and further calculates the ratio of the average A2 to the average A4. The generating function 213 further generates the X-ray image I11 corresponding to the brightness level of the region R2 in the fluoroscopic image I4 by multiplying the pixel values of the pixels in the X-ray image I9 by the calculated ratio. After that, the generating function 213 generates a subtraction image I6 by calculating the difference between the region of interest R1 in the fluoroscopic image I4 and the region corresponding to the region of interest R1 in the X-ray image I10 and calculating the difference between the region R2 in the fluoroscopic image I4 and the region corresponding to the region R2 in the X-ray image I11. In that situation, the X-ray image I9 will be referred to as the first X-ray image, whereas the X-ray image I10 will be referred to as the second X-ray image, whereas the X-ray image I11 will be referred to as the third X-ray image, whereas the fluoroscopic image I4 will be referred to as a fourth X-ray image.

Further, for example, from the X-ray image I9, the generating function 213 generates an X-ray image I12 corresponding to the brightness level of the region of interest R1 and the brightness level of the region R2 in the fluoroscopic image I4, as an X-ray image to be used for calculating the difference from the fluoroscopic image I4.

In one example, toe generating function 213, at first, obtains the average A1 of the pixel values of the pixels included in the region of interest R1 and the average A2 of the pixel values of the pixels included in the region R2, on the basis of the position information of the region of interest R1 in the fluoroscopic image I4. Further, the generating function 213 obtains the average A3 of the pixel values of the pixels included in the region corresponding to the region of interest R1 in the X-ray image I9 and the average A4 of the pixel values of the pixels included in the region corresponding to the region R2 in the X-ray image I9. Further, the generating function 213 generates the X-ray image I12 corresponding to the brightness level of the region of interest R1 and the brightness level of the region R2, by multiplying the pixel values of the pixels included in the region of interest R1 in the X-ray image I9 by the ratio of the average A1 to the average A3 and multiplying the pixel values of the pixels included in the region R2 of the X-ray image I9 by the radio of the average A2 to the average A4. After that, the generating function 213 generates a subtraction image I6 by calculating the difference between the X-ray image I12 and the fluoroscopic image I4. In that situation, the X-ray image I9 will be referred to as the first X-ray image, whereas the X-ray image I12 will be referred to as the second X-ray image, whereas the fluoroscopic image I4 will be referred to as the third X-ray image.

Further, in the embodiments described above, the example is explained in which the fluoroscopic image I4 is acquired by using the X-rays in the two types of radiation doses, namely the first radiation dose and the second radiation dose. However, possible embodiments are not limited to this example. For instance, the fluoroscopic image I4 may be acquired by using X-rays in three or more types of radiation doses. In that situation, for example, the acquiring function 211 acquires X-rays images each by radiating X-rays onto the entire area thereof in a different one of the mutually-different radiation doses used for the fluoroscopic image I4. Further, the obtaining function 212 obtains a distribution of the radiation doses in the fluoroscopic image I4. The generating function 213 further generates a wire mask image I5 on the basis of the X-ray images acquired by using the mutually-different radiation doses and the distribution of the radiation doses in the fluoroscopic image I4. After that, the generating function 213 generates a subtraction image by calculating the difference between the fluoroscopic image I4 acquired by using the X-rays in the three or more types of radiation doses and the wire mask image I5. The display controlling function 214 is thus able to implement the fluoroscopy road map function.

The constituent elements of the apparatuses and the devices according to the embodiments described above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is possible to realize the image processing method explained in any of the embodiments above, by causing a computer such as a personal computer or a workstation to execute an image processing computer program (hereinafter, "image processing program") prepared in advance. It is possible to distribute the image processing program via network such as the Internet. Further, the image processing program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

According to at least one aspect of the embodiments described above, it is possible to improve the efficiency of the intervention treatment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising processing circuitry configured:
- to acquire a first X-ray image on a basis of X-rays radiated onto a subject in a first radiation dose;
- to acquire a second X-ray image on a basis of X-rays radiated onto the subject in a second radiation dose lower than the first radiation dose;
- to acquire a third X-ray image on a basis of X-rays radiated onto a region of interest of the subject into which a medical device is inserted and onto a region other than the region of interest, in mutually-different radiation doses;
- to obtain position information of the region of interest in the third X-ray image;
- to obtain positions corresponding to the region of interest in the first X-ray image and in the second X-ray image on a basis of the position information; and
- to generate a subtraction image by calculating a difference between the region of interest in the third X-ray image and a region corresponding to the region of interest in the first X-ray image and calculating a difference between a region other than the region of interest in the third X-ray image and a region corresponding to the region other than the region of interest in the second X-ray image.

2. The X-ray diagnosis apparatus according to claim 1, wherein the processing circuitry is configured to obtain the position information from an X-ray image acquired on a basis of X-rays radiated onto the region of interest and the region other than the region of interest, in mutually-different radiation doses.

3. The X-ray diagnosis apparatus according to claim 2, wherein the processing circuitry is configured to obtain the position information from the third X-ray image.

4. The X-ray diagnosis apparatus according to claim 1, wherein the processing circuitry is configured to obtain the position information on a basis of a distribution of X-ray radiation doses for the subject.

5. The X-ray diagnosis apparatus according to claim 1, further comprising a filter that is configured to attenuate X-rays, has a first region to attenuate X-rays passing therethrough as well as one selected from between an opening to pass X-rays without attenuating the X-rays and a second region to attenuate passing X-rays at an attenuation rate lower than an attenuation rate of the X-rays passing through the first region, and is capable of moving the one selected from between the opening and the second region, wherein the processing circuitry is further configured:
- to control the moving of the one selected from between the opening and the second region, and
- to acquire the third X-ray image on a basis of X-rays emitted from an X-ray tube and subsequently radiated onto the region of interest via the one selected from between the opening and the second region and X-rays emitted from the X-ray tube and subsequently radiated onto the region other than the region of interest via the first region.

6. The X-ray diagnosis apparatus according to claim 5, wherein the processing circuitry is configured to obtain the position information on a basis of a position of the one selected from between the opening and the second region of the filter.

7. The X-ray diagnosis apparatus according to claim 1, wherein the processing circuitry is further configured:
- to acquire a blood vessel image by calculating a difference between an X-ray image based on X-rays that have passed through the subject before a contrast agent is injected and an X-ray image based on X-rays that have passed through the subject after the contrast agent is injected,
- to generate a superimposed image by superimposing the subtraction image and the blood vessel image on each other, and
- to cause the superimposed image to be displayed on display.

8. The X-ray diagnosis apparatus according to claim 1, wherein the processing circuitry is further configured:
- to acquire a blood vessel image by calculating a difference between an X-ray image based on X-rays that have passed through the subject before a contrast agent is injected and an X-ray image based on X-rays that have passed through the subject after the contrast agent is injected,
- to generate a superimposed image by superimposing an X-ray image based on X-rays that have passed through the subject, the subtraction image, and the blood vessel image on one another, and
- to cause the superimposed image to be displayed on display.

9. The X-ray diagnosis apparatus according to claim 7, wherein the processing circuitry is configured:
- to acquire a blood vessel image by calculating a difference between a fluoroscopic image based on X-rays that have passed through the subject before a contrast agent is injected and a fluoroscopic image based on X-rays that have passed through the subject after the contrast agent is injected, and
- to generate the subtraction image by using the fluoroscopic image based on the X-rays that have passed through the subject before the contrast agent is injected as the first X-ray image.

10. The X-ray diagnosis apparatus according to claim 1, wherein the processing circuitry is configured to acquire the third X-ray image on a basis of X-rays radiated onto the region of interest of the subject into which the medical device is inserted in the first radiation dose and radiated onto the region other than the region of interest in the second radiation dose.

11. An X-ray diagnosis apparatus comprising processing circuitry configured:
- to acquire a first X-ray image based on X-rays radiated onto a subject;
- to generate a second X-ray image and a third X-ray image from the first X-ray image;
- to acquire a fourth X-ray image on a basis of X-rays radiated onto a region of interest of the subject into which a medical device is inserted and onto a region other than the region of interest, in mutually-different radiation doses; and
- to obtain position information of the region of interest in the fourth X-ray image, wherein the processing circuitry is configured:
- to generate, on a basis of the position information, the second X-ray image in correspondence with a brightness level of the region of interest in the fourth X-ray image and the third X-ray image in correspondence with a brightness level of the region other than the region of interest in the fourth X-ray image, and to generate a subtraction image by calculating a difference between the region of interest in the fourth X-ray image and a region corresponding to the region of interest in the second X-ray image and calculating a difference between the region other than the region of interest in the fourth X-ray image and a region corresponding to the region other than the region of interest in the third X-ray image.

12. The X-ray diagnosis apparatus according to claim 11, wherein the processing circuitry is configured to obtain the position information from an X-ray image acquired on a basis of X-rays radiated onto the region of interest and the region other than the region of interest, in mutually-different radiation doses.

13. The X-ray diagnosis apparatus according to claim 12, wherein the processing circuitry is configured to obtain the position information from the fourth X-ray image.

14. The X-ray diagnosis apparatus according to claim 11, wherein the processing circuitry is configured to obtain the position information on a basis of a distribution of X-ray radiation doses for the subject.

15. The X-ray diagnosis apparatus according to claim 11, further comprising a filter that is configured to attenuate X-rays, has a first region to attenuate X-rays passing therethrough as well as one selected from between an opening to pass X-rays without attenuating the X-rays and a second region to attenuate passing X-rays at an attenuation rate loner than an attenuation rate of the X-rays passing through the first region, and is capable of moving the one selected from between the opening and the second region, wherein the processing circuitry is further configured:

to control the moving of the one selected from between the opening and the second region, to acquire the fourth X-ray image on a basis rays emitted from an X-ray tube and subsequently radiated onto the region of interest via the one selected from between the opening and the second region and X-rays emitted from the X-ray tube and subsequently radiated onto the region other than the region of interest via the first region, and to obtain the position information on a basis of a position of the one selected from between the opening and the second region of the filter.

16. An X-ray diagnosis apparatus comprising processing circuitry configured:

to acquire a first X-ray image based on X-rays radiated onto a subject;

to generate a second X-ray image from the first X-ray image;

to acquire a third X-ray image on a basis of X-rays radiated onto a region of interest of the subject into which a medical device is inserted and onto a region other than the region of interest, in mutually-different radiation doses; and to obtain position information of the region of interest in the third X-ray image, wherein the processing circuitry is configured:

to generate, on a basis of the position information, the second X-ray image by adjusting a brightness level of a region corresponding to the region of interest in the first X-ray image in correspondence with a brightness level of the region of interest in the third X-ray image and adjusting a brightness level of a region corresponding to the region other than the region of interest in the first X-ray image in correspondence with a brightness level of the region other than the region of interest in the third X-ray image, and to generate a subtraction image by calculating a difference between the second X-ray image and the third X-ray image.

17. The X-ray diagnosis apparatus according to claim 16, wherein the processing circuitry is configured to obtain the position information from an X-ray image acquired on a basis of X-rays radiated onto the region of interest and the region other than the region of interest, in mutually-different radiation doses.

18. The X-ray diagnosis apparatus according to claim 17, wherein the processing circuitry is configured to obtain the position information from the third X-ray image.

19. The X-ray diagnosis apparatus according to claim 16, wherein the processing circuitry is configured to obtain the position information on a basis of a distribution of X-ray radiation doses for the subject.

20. The X-ray diagnosis apparatus according to claim 16, further comprising a filter that is configured to attenuate X-rays, has a first region to attenuate X-rays passing therethrough as well as one selected from between an opening to pass X-rays without attenuating the X-rays and a second region to attenuate passing X-rays at an attenuation rate lower than an attenuation rate of the X-rays passing through the first region, and is capable of moving the one selected from between the opening and the second region, wherein the processing circuitry is further configured:

to control the moving of the one selected from between the opening and the second region, to acquire the third X-ray image on a basis of X-rays emitted from an X-ray tube and subsequently radiated onto the region of interest via the one selected from between the opening and the second region and X-rays emitted from the X-ray tube and subsequently radiated onto the region other than the region of interest via the first region, and to obtain the position information on a basis of a position of the one selected from between the opening and the second region of the filter.

* * * * *